(12) United States Patent
Housley

(10) Patent No.: US 11,026,842 B2
(45) Date of Patent: *Jun. 8, 2021

(54) METHOD OF PROVIDING AGENTS TO THE COCHLEA

(71) Applicant: NewSouth Innovations Pty Limited, New South Wales (AU)

(72) Inventor: Gary David Housley, Connells Point (AU)

(73) Assignee: NewSouth Innovations Pty Limited, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/387,344

(22) Filed: Dec. 21, 2016

(65) Prior Publication Data

US 2017/0173323 A1 Jun. 22, 2017

Related U.S. Application Data

(63) Continuation of application No. 14/145,673, filed on Dec. 31, 2013, now Pat. No. 9,533,138, which is a
(Continued)

(30) Foreign Application Priority Data

Jul. 15, 2009 (AU) .................................. 2009903320

(51) Int. Cl.
*A61F 11/00* (2006.01)
*A61N 1/04* (2006.01)
(Continued)

(52) U.S. Cl.
CPC .......... *A61F 11/00* (2013.01); *A61K 41/0047* (2013.01); *A61K 48/0075* (2013.01);
(Continued)

(58) Field of Classification Search
None
See application file for complete search history.

(56) References Cited

U.S. PATENT DOCUMENTS

| | | | |
|---|---|---|---|
| 5,702,359 A | 12/1997 | Hofmann et al. | |
| 6,972,013 B1 | 12/2005 | Zhang et al. | |

(Continued)

FOREIGN PATENT DOCUMENTS

| WO | 9639226 | 12/1996 |
|---|---|---|
| WO | WO-98/000014 A1 | 1/1998 |

(Continued)

OTHER PUBLICATIONS

Li et al., Electroporation Protocols Preclinical and Clinical Gene Medicine, in Methods in Molecular Biology. Humana Press, 2008, pp. 1-524 (Year: 2008).*

(Continued)

*Primary Examiner* — Christopher M Babic
*Assistant Examiner* — Arthur S Leonard
(74) *Attorney, Agent, or Firm* — Schwegman Lundberg & Woessner, P.A.

(57) ABSTRACT

Provided is a method of transfecting cells of the cochlea with an agent by electroporation, and in certain embodiments using a cochlear implant to provide at least one electroporation electrode.

15 Claims, 8 Drawing Sheets

Related U.S. Application Data continuation of application No. 13/384,020, filed as application No. PCT/AU2010/000899 on Jul. 15, 2010, now abandoned.

(51) Int. Cl.
  *A61N 1/05* (2006.01)
  *A61N 1/32* (2006.01)
  *A61K 41/00* (2020.01)
  *A61K 48/00* (2006.01)
  *A61M 37/00* (2006.01)

(52) U.S. Cl.
  CPC ......... *A61N 1/0412* (2013.01); *A61N 1/0541* (2013.01); *A61N 1/327* (2013.01); *A61M 2037/0007* (2013.01)

(56) References Cited

U.S. PATENT DOCUMENTS

| | | | |
|---|---|---|---|
| 7,315,763 | B2 | 1/2008 | Kuzma et al. |
| 7,317,944 | B1 | 1/2008 | Overstreet |
| 7,319,906 | B2 | 1/2008 | Kuzma et al. |
| 7,340,308 | B1 | 3/2008 | Clopton et al. |
| 7,349,744 | B2 | 3/2008 | Dadd et al. |
| 7,367,992 | B2 | 5/2008 | Dadd |
| 7,406,352 | B2 | 7/2008 | Gibson |
| 7,451,000 | B2 | 11/2008 | Gibson et al. |
| 7,456,012 | B2 | 11/2008 | Ryttsen et al. |
| 7,879,610 | B1 | 2/2011 | Heller et al. |
| 9,533,138 | B2 | 1/2017 | Housley |
| 2003/0203482 | A1 | 10/2003 | Kil et al. |
| 2005/0256560 | A1* | 11/2005 | Lenarz .............. A61F 11/00 607/137 |
| 2005/0281786 | A1 | 12/2005 | Poulsen et al. |
| 2006/0247735 | A1 | 11/2006 | Honert |
| 2008/0214986 | A1 | 9/2008 | Ivorra et al. |
| 2009/0076160 | A1* | 3/2009 | Lendvai ............ A61K 31/135 514/647 |
| 2012/0191032 | A1 | 7/2012 | Housley |
| 2014/0194807 | A1 | 7/2014 | Housley |

FOREIGN PATENT DOCUMENTS

| | | |
|---|---|---|
| WO | WO-0067837 A1 | 11/2000 |
| WO | WO-2001012115 A1 | 2/2001 |
| WO | WO-2003/063543 A2 | 7/2003 |
| WO | 03072193 | 9/2003 |
| WO | WO-2007/137335 A1 | 12/2007 |
| WO | WO-2010/008627 A1 | 1/2010 |

OTHER PUBLICATIONS

Clark et al., Design and fabrication of the banded electrode array. Ann N Y Acad Sci; 1983;405:191-201. (Year: 1983).*

"European Application Serial No. 10799287.7, Communication Pursuant to Article 94(3) dated May 11, 2017", (Dec. 14, 2017), 10 pgs.

"U.S. Appl. No. 13/384,020, Response filed Mar. 13, 2013 to Non Final Office Action dated Nov. 15, 2012", 13 pgs.

"U.S. Appl. No. 13/384,020, Final Office Action dated Jul. 1, 2013", 17 pgs.

"U.S. Appl. No. 13/384,020, Non Final Office Action dated Nov. 15, 2012", 11 pgs.

"U.S. Appl. No. 13/384,020, Response filed Oct. 1, 2012 to Restriction Requirement dated Aug. 17, 2012", 5 pgs.

"U.S. Appl. No. 13/384,020, Restriction Requirement dated Aug. 17, 2012", 8 pgs.

"U.S. Appl. No. 14/145,673, Final Office Action dated May 31, 2016", 19 pgs.

"U.S. Appl. No. 14/145,673, Non Final Office Action dated Nov. 24, 2015", 14 pgs.

"U.S. Appl. No. 14/145,673, Notice of Allowance dated Aug. 26, 2016", 9 pgs.

"U.S. Appl. No. 14/145,673, Response filed Feb. 22, 2016 to Non Final Office Action dated Nov. 24, 2015", 8 pgs.

"U.S. Appl. No. 14/145,673, Response filed Jul. 28, 2016 to Final Office Action dated May 31, 2016", 6 pgs.

"U.S. Appl. No. 14/145,673, Response filed Aug. 27, 2015 to Restriction Requirement dated Feb. 27, 2015", 5 pgs.

"U.S. Appl. No. 14/145,673, Restriction Requirement dated Feb. 27, 2015", 6 pgs.

"International Application No. PCT/AU2010/000899, International Preliminary Report on Patentability completed Jun. 7, 2011", (Jun. 7, 2011), 5 pgs.

"International Application No. PCT/Au2010/000899, International Search Report dated Sep. 2, 2010", (Sep. 2, 2010), 4 pgs.

"Understanding the cochlear implant", Biomed Brown Univeristy, Retrieved From the internet: <http://biomed.brown.edu/Courses/B1108/2006-108websites/group10cochlearimplant/pages/electrodearray.html>, (May 2006), 1-5.

Badi, A. N., et al., "A Technique for Implantation of a 3-Dimensional Penetrating Electrode Array in the Modiolar Nerve of Cats and Humans", *Arch Otolaryngol Head Neck Surg* 128(9), (2002), 1019-1025.

Brigande, John V., et al,, "Electroporation-Mediated Gene Transfer to the Developing Mouse", *Methods Mol Biol.*, 493, (2009), 125-139.

Cogan, Stuart F., "Neural Stimulation and Recording Electrodes", *Annu. Rev. Biomed. Eng.* 2008, 10, (2008), 37 pgs.

Dabdoub, A., et al., "Sox2 signaling in prosensory domain specification and subsequent hair cell differentiation in the developing cochlea.", *Proc Natl Acad Sci USA*, 105(47), (2008), 18396-183401.

Gubbels, Samuel P., et al., "Functional auditory hair cells produced in the mammalian cochlea by in utero gene transfer", *Nature* 455(7212), (2008), 537-541.

Kawamoto, Kohei, et al., "Antioxidant Gene Therapy Can Protect Hearing and Hair Cells from Ototoxicity", *Molecular Therapy* 9(2). (Feb. 2004), 173-181.

Keithley, Elizabeth M., et al., "Effects of a hair cell transcription factor Brn-3.1. gene deletion on Effects of a hair cell transcription factor Brn-3.1, gene delection on homozygous and heterozygous mouse cochleas in adulthood and aging.", *Hearing Research*, 134(1-2), (1999), 71-76.

Liu, Yuhe, et al., "Promoter effects of adeno-associated viral vector for transgene expression in the cochlea in vivo", *Experimental and Molecular Medicine*, 39(2), (Apr. 2007), 170-175.

Mencía, Angeles, et al., "Mutations in the seed region of human miR-96 are responsible for nonsyndromic progressive hearing loss", *Nature Genetics*, 41(5), (2009), 609-613.

Mencía, Angeles, et al., "Mutations in the seed region of human miR-96 are responsible for nonsyndromic progressive hearing loss", *Nature Genetics*, 41(5), Supporting Information, (2009), 15 pgs.

Paasche, G., et al., "Technical Report: Modification of a Cochlear Implant Electrode for Drug Delivery to the Inner Ear", *Otology & Neurology*, 24(2), (2003), 222-227.

Pinyon, J. L., et al., "Close-field electrode gene delivery using the cochlear implant electrode array enhances the bionic ear", *Science Translational Medicine*, 6(233), (2014), 1-12.

Prado-Guitierrez, et al., "Effect of Interphase Gap and Pulse Duration on Electrically Evoked Potentials Is Correlated With Auditory Nerve Survival", *Hear Res* 215(1-2), (May 2006), 47-55.

Rols, Marie-Pierre, "Electropermeabilization, a physical method for the delivery of therapeutic molecules into cells", *Biochimica et Biophysica Acta* 1758, (2006), 423-428.

Salt, Alec N., "The Cochlear Fluids: Perilymph and Endolymph", In: *Neurobiology of Hearing: The Cochlea*, Altschuler, R. A., etal, Editors, Raven Press, New York, NY, (1968), 109-122.

Stone, Ida M., et al., "Adeno-associated Virus-Mediated Gene Transfer to Hair Cells and Support Cells of the Murine Cochlea", *Molecular Therapy*, 11(6), (2005), 843-884.

Van Der Wees, Jacqueline, et al,. "Hearing loss following Gata3 haploinsufficiency is caused by cochlear disorder", *Neurobiology of Disease*, 16, (2004), 169-178.

(56) References Cited

OTHER PUBLICATIONS

Wang, L., et al., "Abstract: Gene Transfer to the Developing Mouse Inner Ear by in vitro Electroporation", *J Vis Exp*. Jun. 30, 2012; (64), (2012), 1 pg.

Xu, Lingfei, et al., "CMV-B-Actin Promoter Directs Higher Expression from an Adeno-Associated Viral Vector in the Liver than the Cytomegalovirus or Elongation Factor 1a Promoter and Results in Therapeutic Levels of Human Factor X in Mice", *Human Gene Therapy*. 12(5), (2001), 563-573.

Browne, Cherylea J, et al., "Mapping of bionic array electric field focusing in plasmid DNA-based gene electrotransfer", Gene therapy 23.4, (2016), 369-379.

Pinyon, Jeremy L., et al., "Close-field electroporation gene delivery using the cochlear implant electrode array enhances the bionic ear", Science translational medicine 6.233, (2014), 233ra54-233ra54.

Sue, Andr, "Electrochemical Safety Studies of Cochlear Implant Electrodes Using the Finite Element Method", The University of Sydney a thesis for doctor's degree, (Mar. 2016), 274 pgs.

Tognola, Gabriella, et al., "Measurement of electrode current pulses from cochlear implants", IEEE transactions on instrumentation and measurement 54.5, (2005), 2105-2112.

Zeng, Fan-Gang, et al., "Cochlear implants: system design, integration, and evaluation", IEEE reviews in biomedical engineering 1, (2008), 115-142.

Zeng, Fan-Gang, et al., "Development and evaluation of the Nurotron 26-electrode cochlear implant system", Hearing research 322, (2015), 188-199.

\* cited by examiner

METHOD OF PROVIDING AGENTS TO THE COCHLEA

PRIORITY CLAIM TO RELATED APPLICATIONS

This application is a continuation of and claims the benefit of priority to U.S. patent application Ser. No. 14/145,673, filed Dec. 31, 2013, which is a continuation of and claims the benefit of priority to U.S. patent application Ser. No. 13/384, 020, filed Jan. 13, 2012, which is a national stage application under 35 U.S.C. §371 of PCT/AU2010/000899, filed Jul. 15, 2010, and published as WO 2011/006204 A1 on Jan. 20, 2011, which claims priority to Australian Application No. 2009903320, filed Jul. 15, 2009, which applications and publication are incorporated herein by reference and made a part hereof in their entirety, and the benefit of priority of each of which is claimed herein.

DESCRIPTION

Technical Field

The present invention relates to a method of providing an agent to cells of the cochlea using electroporation. The method has particular application in supporting the survival or neurite growth of spiral ganglion cells in subjects having a cochlear implant or intending to undergo a cochlear implant procedure.

Background Art

Sensori-neural deafness arises from the loss of hair cells found within the cochlea, the sensory receptors of the auditory system. This loss of hair cells can lead to degeneration of peripheral processes and death of spiral ganglion neurons which rely on hair cells for stimulus and trophic support. The spiral ganglion neurons reside within Rosenthal's canal in the cochlea, with peripheral neurite processes connecting to the sensory hair cells, and central axons to the cochlear nucleus in the brainstem. Thus the spiral ganglion neurons form the cochlear or auditory nerve which receives auditory stimuli from the auditory receptors and transmit sound information to the brain. The auditory output carried by the cochlear nerve is intrinsically tonotopically mapped, with the basal region of the cochlea being more sensitive to the highest frequency sounds and progressively lower frequencies being encoded by more apical regions of the cochlea.

The cochlear implant is a highly successful application of bionic engineering which can restore a degree of hearing to many deaf subjects. Implants are also being provided to patients with residual low frequency hearing, where the implant provides access to the higher frequency sounds. Cochlear implants act by bypassing the cochlear hair cells and directly electrically stimulating remnant spiral ganglion nerve cell bodies of the cochlear nerve. Accordingly, there are advantages where a cochlear implant is used, for the subject to retain as many cochlear nerve fibres as possible to facilitate the neural transmission of auditory signals to the brain, and to ensure that nerve fibres are present in proximity to the series of electrodes of the cochlear implant.

The implantation procedure may damage a proportion of remnant nerve fibres, nerve cell bodies, and sensory hair cells in the subject's cochlea, and so in subjects with only marginal remnant innervation it is important to maintain as many functional neurons as possible following implantation. Cochlear implants which provide therapeutic support to cochlear tissues following implantation are being investigated. Some strategies for therapeutic support of cochlear tissues involve the use of continuous (tonic) electrical stimulation of spiral ganglion cells to promote the survival of remnant spiral ganglion cells. Other experimental strategies being considered involve direct injection of neurotrophic molecules into the cochlea at the time of implantation. The use of cochlear implants which comprise a drug delivery channel or an ensheathing matrix which provides passive diffusion of agents to surrounding cochlear tissue has also been proposed. These approaches, however, only provide a short-acting delivery of agent to cochlea, thus limiting the degree to which the agents may provide support to the cochlear tissue. The use of encapsulated cells which can be placed within the cochlea to secrete neuroactive molecules is also under investigation as a means of providing longer term therapeutic support to cochlear nerve cells.

Other proposed therapeutic approaches to supporting cochlear neural function utilize gene therapy. These approaches focus on the use of viral-vector based transformation of cochlear tissues, as these techniques are generally considered efficient delivery systems for cell transformation. Viral-based delivery systems are however limited by the lack of site-specific control of the gene delivery, resulting in a dispersed and largely uncontrolled transfection of cells throughout the tissue exposed to the virus, such as cells lining the scala tympani. In addition, the potential for causing undesirable immunological reactions to the viral vector constructs inhibits the immediate translation of this research into clinical use in human subjects.

There is therefore a need for techniques which allow the introduction of genetic constructs to the cochlea and which substantially overcome or ameliorate at least one or more of the above disadvantages.

SUMMARY

Provided herein is a method of transfecting cells with an agent by electroporation within a cochlea of a subject to receive a cochlear implant, the method comprising introducing at least one electrode into the cochlea, providing the agent to the cochlea, and providing at least one second electrode, and then providing an electroporation electric field between the at least one electrode and the at least one second electrode and thereby transfecting cells with the agent. Certain embodiments of the present invention are based on the recognition that a cochlear implant may be modified to deliver an electrical signal of sufficient strength and amplitude to result in the transduction of an agent, such as a nucleic acid molecule into cochlear tissues, such as mesenchymal cells of the scala tympani, by electroporation.

Described herein are methods for directed gene delivery by transfecting cells close to the cochlear implant electrode array using electroporation. This provides, for example, nucleic acid molecule delivery to cells close to the cochlear implant within the cochlea, which potentially offers an enhancement to the subsequent performance of the cochlear implant neural prosthesis.

Accordingly, in one aspect there is provided a method of transfecting cells with an agent by electroporation within a cochlea of a subject, the method comprising introducing a cochlear implant which comprises at least one electrode into the cochlea, providing the agent to the cochlea, and providing at least one second electrode, and then providing an electroporation electric field between the at least one electrode and the at least one second electrode and thereby transfecting cells with the agent.

In particular embodiments the agent comprises or consists of a nucleic acid molecule. The nucleic acid molecule may encode a neurotrophic factor for peripheral sensory neurons, and in particular embodiments the nucleic acid molecule encodes a neurotrophic factor for spiral ganglion cells. In particular embodiments the nucleic acid molecule encodes a transcription factor which promotes the expression of a neurotrophic factor. In particular embodiments the nucleic acid molecule encodes one or more therapeutic molecules for spiral ganglion cells. In particular embodiments the nucleic acid molecule decreases the expression of a transcription factor within mesenchymal cells of the scala tympani or scala vestibuli, wherein expression of the transcription factor inhibits the expression of a neurotrophic factor for spiral ganglion cells by the mesenchymal cell.

Also provided is the use of a nucleic acid molecule which encodes a neurotrophic factor for spiral ganglion cells or which encodes a transcription factor which promotes the expression of a neurotrophic factor for spiral ganglion cells for transfecting a cell of a cochlea of a subject in situ by electroporation.

The neurotrophic factor may be selected from any one of Neurotrophin-3, Neurotrophin-3 precursor molecule, Neurotrophin 4/5, Nerve growth factor, Brain-derived neurotrophic factor, glial cell line-derived neurotrophic factor, ciliary neurotrophic factor and Activity dependent neurotrophic factor.

In particular embodiments the cells are cells of the scala tympani or scala vestibuli, such as mesenchymal cells.

In particular embodiments, the subject is a human.

BRIEF DESCRIPTION OF THE DRAWINGS

Certain embodiments of the present invention will now be described, by way of example only, with reference to the accompanying drawings wherein:

FIG. 5A illustrates an "alternative polarity" configuration in which neighbouring nodes are of opposite polarity. In this illustration the electrode is shown for DC stimulation, but this and other configurations illustrated in this figure would be compatible with other electroporation waveforms. FIG. 5B illustrates a "distributed current return electrodes" configuration for the electroporation mode of a cochlear implant, with a preponderance of current return electrode nodes and a smaller number of current delivery electrode nodes located, for example, at the proximal and distal ends of the electrode. FIGS. 5C and 5C illustrate two configurations in which electrodes labelled in black are dedicated for electroporation mode only and are used for charge delivery. In FIG. 5C the dedicated electroporation current delivery electrodes are used in conjunction with the conventional implant electrode nodes for current return. In FIG. 5D dedicated electroporation current delivery and return electrodes are provided. FIG. 5E illustrates a configuration utilising the integrated electrode array of the cochlear prosthesis and a separate "return" electrode. The external return electrode may be provided to complete the circuit for electroporation using the prosthetic electrode array for delivery of the electroporation therapeutic molecules to the cochlea. The return electrode may be inserted into the cochlear scala vestibuli, if the primary array is placed into scala tympani, or vice versa. Alternatively the return electrode may be placed into the cochlear modiolus, or external to the cochlea. The polarity of the cochlear electrode and the separate electrode may be swapped from the polarity illustrated herein, or the polarity may be reversed one or more times during electroporation. A separate return electrode may also be used in conjunction with a transient electrode array for electroporation-based delivery of an agent, prior to implantation of the cochlear prosthetic electrode array.

DESCRIPTION OF EMBODIMENTS

Figure 1:
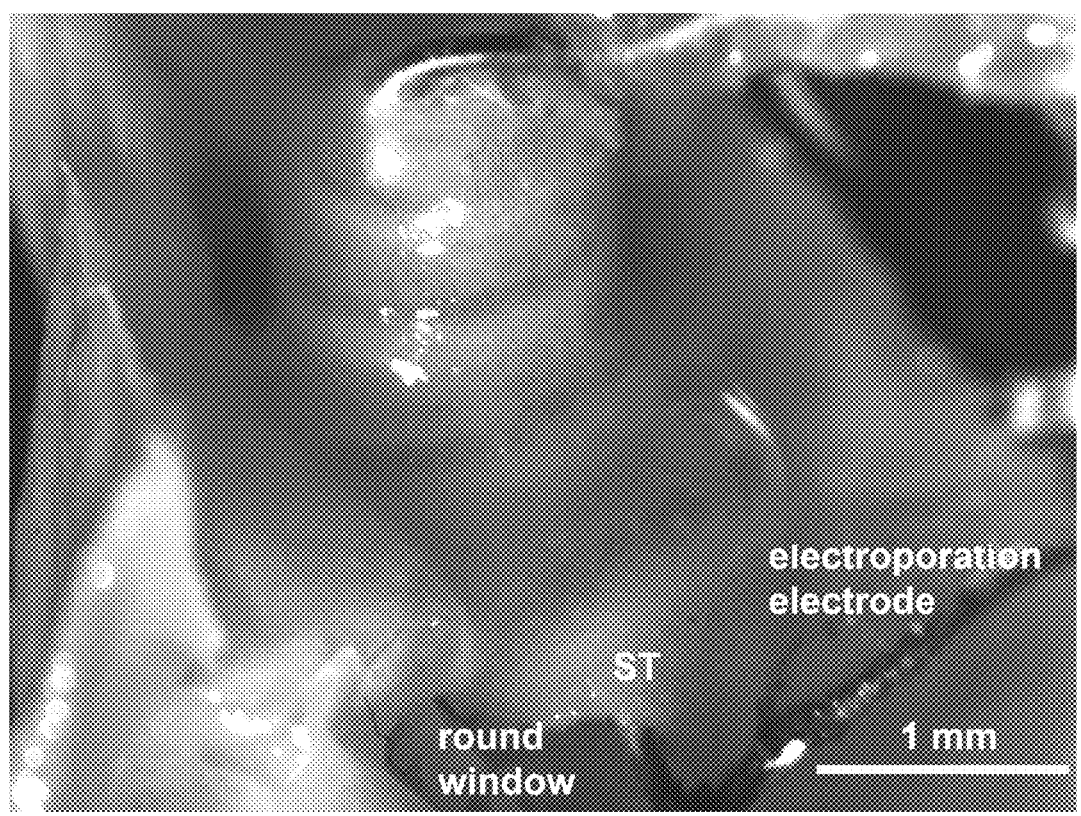
FIG. 1 shows a photograph of an isolated cochlea from an adult guinea-pig demonstrating the electrode configuration used for electroporation gene delivery. The image shows placement of a shaped electroporation electrode through the round window membrane and into the basal turn scala media compartment (simulating the cochlear implant electrode prosthesis), and an apical fenestration with a reference second electrode.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, reference to "a" or "one" element does not exclude the plural, unless context determines otherwise. For instance, reference to "a nucleic acid molecule" should not be read as excluding the possibility of multiple nucleic acid molecules.

As described herein there is provided a method of transfection by electroporation using a cochlear implant for delivery of an agent, such as a nucleic acid molecule, to cells of the cochlea. By relying on electroporation techniques rather than viral mediated transfection it is possible to deliver a wide range of agents, such as naked nucleic acid molecules, to cochlear cells. In addition, by utilising one of the perceived limitations of in vivo electroporation techniques, that is that the efficiency of transfection drops off rapidly as the distance from the electrodes increases, the methods described herein offer a previously unrecognised advantage in the cochlear implant application, as the use of electroporation mediated transfection constrains transfection to the tissue immediately adjacent to the electrode, allowing relatively precise localisation of delivery of the agent only to cochlear cells in the immediate vicinity of the cochlear implant. Typically, only cells within 300 μm of the electrode will be transfected.

One limitation of the operation of cochlear implants in present use is the minimum distance which is employed between the implant electrodes. The cochlea implant is located within the scala tympani fluid compartment and the spiral ganglion cell auditory neurons lie within Rosenthal's canal, the auditory neuron processes having largely retracted following loss of the sensory hair cells. The distance between the implant and the closest processes of auditory neurons is sufficient that the number of electrodes present in an implant, and hence the number of different frequency/intensity bands provided by the implant to the subject's auditory system, is limited by the current spread.

The methods described herein allow the use of gene therapy which may, for example, enhance the expression of spiral ganglion cell trophic molecules, such as brain-derived neurotrophic factor, in cochlear cells which lie close to the cochlear implant. This is proposed to be beneficial to the function of the cochlear implant by promoting spiral ganglion cell neurite outgrowth specifically towards the transformed cells, which in turn bring the spiral ganglion neuron processes in close proximity to the cochlear implant electrodes. By providing spiral ganglion neurite outgrowth close to the position of the cochlear implant, the functionality of the cochlear implant may be improved by lowering the required stimulation currents. The use of lowered stimulation currents may enable the electrode design of the cochlear implant to include a higher density of electrodes when working as a bionic ear, thus also improving the auditory information density that can be delivered to the cochlear nerve.

Subject

The present invention contemplates the transfection of cells of the cochlea with an agent by electroporation which utilises an electrode forming part of a cochlear implant.

Where the methods described herein are intended for therapeutic purposes the cochlea may be present in situ within a live subject. Where the methods described herein are intended for experimental or research purposes the cochlea may be present in situ within a live subject or may be substantially intact but isolated from the subject. A "subject" refers to any animal with a cochlea (e.g., a mammal), including, but not limited to any one of humans, non-human primates, rodents, and the like, which is or is to be the recipient of a cochlear implant. Typically, the terms "subject" and "patient" are used interchangeably herein. Typically the subject is a human subject.

As used herein, the term "non-human animals" refers to non-human vertebrate animals including, but not necessarily limited to, rodents, non-human primates, ovines, bovines, ruminants, lagomorphs, porcines, caprines, equines, canines, felines, aves, etc.

The cells which are transfected by the methods described herein will be cells lying within 300 μm to an electrode of the cochlear implant. Typically, but not necessarily exclusively, cells transfected by the methods described herein will be cochlear mesenchymal cells.

In particular embodiments the subject's cochlea is a mature cochlea, which as used herein refers to a developmental stage of the cochlea within which air-borne sound transduction takes place. In rodents such as rats, mice and guinea pigs, this typically occurs around one week after birth. In humans air-borne sound transduction commences at birth.

Agents

Nucleic Acid Molecules

In certain embodiments, the agent may consist of a nucleic acid molecule. In certain embodiments the agent may comprise a nucleic acid molecule, in which case the agent may, for example, also comprise molecules which enhance the stability or transfection efficiency of the nucleic acid molecule, such as chitosan, and/or may also comprise non nucleic acid molecules such as small neuroprotective peptides.

As used herein, the term "nucleic acid molecule" refers to any nucleic acid containing molecule, including but not limited to DNA or RNA molecules. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxymethyl)uracil, 5-carboxymethylaminomethyl-2-thiouracil, 5-carboxymethylaminomethyluracil-, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine, provided that the analog is not toxic to cochlear cells. A nucleic acid molecule may include modifications designed to improve delivery into cells, stability once inside a cell, and/or binding to the appropriate intracellular target.

The nucleic acid molecule may be an oligonucleotide or a polynucleotide. In particular embodiments the nucleic acid molecule is naked DNA, such as cDNA, or naked RNA. In particular embodiments the use of encapsulated DNA or RNA, such as polynucleotides present in liposomes or microspheres is also contemplated, particularly where such encapsulation improves the stability of the agent or the efficiency of transfection by electroporation. The use of encapsulated DNA or RNA may offer a less advantageous embodiment if encapsulation allows transfection of cells which are distant to the electrode to take place. It will be understood by a person skilled in the art that particles may be mixed with the nucleic acid molecule to condense the nucleic acid molecule, which may provide increased transduction efficiency.

(a) Nucleic Acid Molecules which Encode a Polypeptide Product

The agent may be a nucleic acid molecule which encodes a polypeptide product. The expression of the encoded polypeptide product promotes a desired outcome, such as promoting or maintaining spiral ganglion cell neurite outgrowth and/or spiral ganglion cell survival.

The encoded polypeptide product may be an endogenous polypeptide to the subject. In certain embodiments the encoded polypeptide product is an exogenous polypeptide.

The nucleic acid molecule which encodes a polypeptide product comprises a coding sequence for a polypeptide product or a precursor polypeptide of the polypeptide product. The polypeptide product may be a full-length polypeptide which occurs in nature, or it may be a portion of a polypeptide which occurs in nature, provided that the desired activity or functional properties (such as receptor binding and/or the ability to induce signal transduction) of the polypeptide product are retained. The nucleic acid molecule may also comprise a sequence located adjacent to the coding sequence on the 5' or 3' end of the coding sequence or on both the 5' and 3' ends for a distance of about 1 kb or more on either end such that the sequence corresponds to the length of a full-length mRNA sequence. Sequences located 5' of the coding region and present on the mRNA are referred to as 5' non-translated sequences. Sequences located 3' or downstream of the coding region and present on the mRNA are referred to as 3' non-translated sequences.

The nucleic acid molecule may comprise a cDNA sequence encoding a polypeptide product. The nucleic acid molecule may comprise a genomic sequence encoding a polypeptide product. A genomic sequence contains the coding region interrupted with non-coding sequences termed "introns" or "intervening regions" or "intervening sequences." Introns are segments of a gene that are transcribed into nuclear RNA (nRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In certain embodiments, the expression of a nucleic acid molecule refers to the process of converting genetic information encoded in the nucleic acid molecule into RNA (including for example mRNA or snRNA) through "transcription" of the nucleic acid molecule (i.e., via the enzymatic action of an RNA polymerase), and for nucleic acid molecules encoding a polypeptide, into a polypeptide product through translation of mRNA. Expression can be regulated at many stages in the process. "Up regulation" refers to regulation that increases the production of expression products (i.e., RNA or protein), while "down regulation" refers to regulation that decreases production. Molecules (e.g., transcription factors) that are involved in up regulation or down regulation are often called "activators" and "repressors" respectively.

In addition to containing introns, genomic forms of a nucleic acid molecule may also include sequences located on both the 5' and 3' end of the sequences that are present on an RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

A nucleic acid molecule may be present in a cDNA, genomic DNA or RNA form. When present in a DNA form, the nucleic acid molecule may be single-stranded (i.e., the sense strand) or double-stranded. Suitable control elements such as enhancers/promoters, splice junctions, polyadenylation signals, etc. may be placed in close proximity to the coding region of the nucleic acid molecule if needed to permit proper initiation of transcription and/or correct processing of the primary RNA transcript. Alternatively, the coding region utilized in expression vectors may contain endogenous enhancers/promoters, splice junctions, intervening sequences, polyadenylation signals, etc. or a combination of both endogenous and exogenous control elements.

A nucleic acid molecule may produce multiple RNA species that are generated by differential splicing of the primary RNA transcript, cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire nucleic acid molecule or portions of the nucleic acid molecule containing sequences found on both cDNAs; the two splice variants are therefore substantially homologous to such a probe and to each other.

The terms "in operable combination," "in operable order," and "operably linked" as used herein refer to the linkage of nucleic acid molecule sequences in such a manner that a nucleic acid molecule capable of directing the transcription of a given sequence and/or the synthesis of a desired polypeptide product is produced. The term also refers to the linkage of amino acid sequences in such a manner so that a functional protein is produced.

In certain embodiments the nucleic acid molecule is provided in the form of "expression vector" or "expression cassette", which as used herein refers to a recombinant DNA molecule containing at least one desired coding sequence and appropriate nucleic acid sequences necessary for the expression of the operably linked coding sequence in a particular host organism. Nucleic acid sequences necessary for expression in eukaryotic cells are known to utilize promoters, enhancers, and termination and polyadenylation signals.

In certain embodiments the nucleic acid molecule may encode a polypeptide product which is expressed episomally, for example when the nucleic acid is presented in the form of a vector, such as a plasmid. The use of a suitable episomal vector provides a means of maintaining a polynucleotide sequence in target cells in high copy number extra-chromosomally, thereby eliminating potential effects of chromosomal integration. In these embodiments, the sequence which encodes the polypeptide product may be associated with a promoter which facilitates transcription of the sequence which encodes the polypeptide product. The promoter may be a constitutive promoter or an inducible promoter. Suitable promoters may include, but are not necessarily limited to a cytomegalovirus (CMV) promoter (see, for example Chen, X., Frisina, R. D., Bowers, W. J., Frisina, D. R., Federoff, H. J. (2001) HSV amplicon-mediated neurotrophin-3 expression protects murine spiral ganglion neurons from cisplatin-induced damage. *Molecular Therapy* 3 (6): 958-63 or Kawamoto, K., Sha. S. H., Minoda, R., Izumikawa. M., Kuriyama, H., Schacht, J., Raphael, Y. (2004) Antioxidant gene therapy can protect hearing and hair cells from ototoxicity. *Molecular Therapy* 9 (2): 173-181, the entire contents of which are incorporated herein by reference). The promoter may comprise a Myosin Vlla (Myo) or neuron specific enolase (NSE) promoter, as these are cell specific transcription regulators for hair cells (Myo) and spiral ganglion neurons (NSE). The promoter may comprise a cytomegalovirus immediate early (IE) enhancer (CMV-IE), or a chicken beta-actin promoter (CAG), or an elongation factor 1alpha promoter (EF-1alpha) or a Rous sarcoma virus promoter (RSV) (see, for example, Liu, Y., Okada, T., Nomoto, T., Ke, X., Kume, A., Ozawa, K., Xiao, S. (2007) Promoter effects of adeno-associated viral vector for transgene expression in the cochlea in vivo. *Exp Mol Med.* 39 (2) 170-175, the entire contents of which are incorporated herein by reference). The promoter may comprise a glial fibrillary acidic protein (GFAP) promoter. The promoter may comprise a CBA promoter, which is a hybrid promoter comprising a sequence from the chicken β-actin promoter and from the CMV promoter.

In certain embodiments the nucleic acid molecule comprises a post-transcriptional regulatory element, for example to enhance expression of the agent, such as the woodchuck hepatitis virus posttranscriptional regulatory element (WPRE) (see, for example Stone, I. M., Lurie, D. I., Kelley, M. W., Poulsen, D. J. (2005) Adeno-associated virus-mediated gene transfer to hair cells and support cells of the murine cochlea. *Mol Ther* 11(6): 843-84 and Xu, L., et al. (2001) CMV-beta-actin promoter directs higher expression from an adeno-associated viral vector in the liver than the cytomegalovirus or elongation factor 1 alpha promoter and results in therapeutic levels of human factor X in mice. *Hum. Gene Ther.* 12: 563-573, the entire contents of which are incorporated herein by reference.)

In certain embodiments the Nrg-ICD enhancer and/or PSD-95 promoter is used for targeting of the expression of agent in spiral ganglion neurons (see for example Bao, J., Lin, H., Ouyang, Y., Lei, D., Osman, A., Kim, T. W., Mei, L., Dai, P., Ohlemiller. K. K., Ambron, R. T. (2004) Activity-dependent transcription regulation of PSD-95 by neuregulin-1 and Eos. *Nature Neuroscience* 7 (11): 1250-8, the entire contents of which is incorporated herein by reference)

In certain embodiments the nucleic acid molecule may be incorporated into the genome of cells, such as mesenchymal cells of the scala tympani or scala vestibuli.

The polypeptide product which is encoded by the nucleic acid molecule may be a neurotrophic factor for spiral ganglion cells or cochlear hair cells. As used herein a "neurotrophic factor" is a polypeptide possessing at least one activity selected from promoting or maintaining neurite outgrowth from spiral ganglion cells and/or directing neurite outgrowth from spiral ganglion cells towards the source of the neurotrophic factor, and/or supporting the survival of spiral ganglion cells, and/or supporting the survival of cochlear hair cells. In a particular embodiment the neurotrophic factor possesses activity in promoting or maintaining neurite outgrowth from spiral ganglion cells and/or directing neurite outgrowth from spiral ganglion cells towards the source of the neurotrophic factor, and/or supporting the survival of spiral ganglion cells. The neurotrophic factor may be encoded as a preprotein, and optionally subsequently processed a mature form. In certain embodiments, the neurotrophic factor may be selected from Neurotrophin-3 (NT-3) or Neurotrophin-3 precursor molecule or a preprotein form thereof (NCBI Accession No. HGNC:8023, Swiss Prot Accession Number P20783) or homologs or human variants thereof; Neurotrophin 4/5 (NT-4/5, NT-4, NT-5, NTF4, NTF5) or a preprotein form thereof ((HGNC:8024), Ensembl accession No. ENSP00000328738, GenBank accession No. AAA60154, version GI:190265) or homologs or human variants thereof; Nerve growth factor (NGF) (NCBI Accession No. NP_002497.2 version GI:70995319) (HGNC:7808), Ensembl assession no. ENSP00000358525), preprotein forms thereof or homologs or human variants thereof; Brain derived neurotrophic factor (BDNF, Brain-derived neurotrophic factor Precursor, Abrineurin) (the preprotein form of which is described in NCBI Accession No. NP_001137277.1 version GI:219842288, UniProtKB/Swiss-Prot Accession No P23560) or homologs or human variants thereof; glial cell line-derived neurotrophic factor (GDNF, glial cell derived neurotrophic factor precursor) (NCBI Accession No. HGNC:4232 (gene) or the preprotein forms as described in NCBI Accession Numbers NP_000505 and NP_000505.1) or homologs or human variants thereof: ciliary neurotrophic factor (CNTF) (NCBI Accession No. NP_000605 version GI:4758020 (HGNC: 2169), UniProtKB/Swiss-Prot Accession No. P26441) or homologs or human variants thereof; Activity dependent neurotrophic factor (ADNF, ADNP1; KIAA0784; ADNP, or Activity-dependent neuroprotector homeobox protein) (Ensembl Accession Numbers: ENSP00000360662, ENSP00000379346, ENSP00000342905, and ENSP00000379349) or homologs or human variants thereof, or fragments thereof, or the ADNF homologues ADNF-9 or the active peptide region with an amino acid sequence of SALLRSIPA, or ADNF-14 (neuropeptide) or the neuroprotective NAP peptide of ADNF with an amino acid sequence of NAPVSIPQ; the cytokine trophic factor leukaemia inhibitory factor (LIF) (NCBI accession No. HGNC:6596 (genomic sequence), UniProtKB/Swiss-Prot Accession No. NP_002300.1 version GI:4504991 (polypeptide), typically in conjunction with a neurotrophin such as NT-3; and Fibroblast growth factor (FGF 1, FGF 2) (NCBI accession No NM_002006 (genomic sequence), UniProtKB/Swiss-Prot Accession No. P09038 (polypeptide)) or homologs or human variants thereof, which is believed to interact with NT3 and to support neurite outgrowth and growth cone development, or in a combination of FGF-2 & GDNF.

The polypeptide product which is encoded may be an Apyrase (IUBMB Enzyme Nomenclature Enzyme classification EC 3.6.1.5), an enzyme which hydrolyses ATP extracellularly and therefore prevents P2X receptor activation which can inhibit neurotrophin-dependent neurite outgrowth. The polypeptide product may be an ectonucleotidase, an enzyme which promotes the production of adenosine, which is neuroprotective via adenosine receptors on spiral ganglion neurons. An example of a suitable ectonucleotidase in human subjects is ectonucleoside triphosphate diphosphohydrolase 2 (ENTPD2) (NCBI Accession no. NM 001246).

The polypeptide product which is encoded by the nucleic acid molecule may be involved in the melanocortin signalling pathway, for example alpha-melanocyte stimulating hormone (alpha-MSH). The melanocortins make up a family of endogenous peptides derived from pro-opiomelanocortin, which bind to five melanocortin receptors (MCRs). Other examples of melanocortins which may be encoded by the nucleic acid molecule include proopiomelanocortin (POMC) or its cleavage products (adrenocorticotropin/beta-lipotropin/alpha-melanocyte stimulating hormone/beta-melanocyte stimulating hormone/beta-endorphin) or precursors of active peptides (for gene NCBI Accession No. HGNC: 9201; for precursor NCBI accession No AAA60140 version GI:190188).

The polypeptide product which is encoded by the nucleic acid molecule may be a morphogen, for example a bone morphogenic protein (BMP), Sonic hedgehog, or Wingless/Wnts.

The polypeptide product which is encoded by the nucleic acid molecule may be an axon guidance factor which is capable of attracting spiral ganglion cell neurites, such as laminin, Netrin-1, an Ephrin, a semaphorin, a Slit such as a 3 slit homolog, slit2 or slit3 or a cytokine such as Leukemia inhibitory factor.

(b) Nucleic Acid Molecules which Modulate Endogenous Gene Expression

In certain embodiments the agent may comprise or consist of a nucleic acid molecule which modulates the expression of an endogenous gene sequence. The modulation of expression of the endogenous gene expression may be a direct regulation of expression, for example by directly modulating transcription or translation of an endogenous gene. The modulation of expression of the endogenous gene by the nucleic acid molecule may be an indirect regulation of expression, for example by expression of a polypeptide by the nucleic acid molecule which in turn modulates the expression of the endogenous gene. An example may be targeted inhibition of adenosine kinase (NCBI accession No HGNC:257 (genomic sequence); NP_001114.2 (polypeptide)), leading to increased extracellular adenosine levels which are neuroprotective.

The modulation of expression of an endogenous gene sequence may be an up regulation of an endogenous gene sequence. For example, the nucleic acid molecule may encode a transcription factor which promotes the expression of an endogenous gene, such as a gene which encodes a neurotrophic factor. The Sox2, Brn-3.1 and Gata 3 transcription factors are examples of this class of cell signalling molecule associated with determination of sensory hair cell, supporting cell and spiral ganglion neuron development and survival in the cochlea (Keithley, E M, Erkman. L., Bennett. T., Lou, L. Ryan, A. F. (1999) Effects of a hair cell transcription factor Brn-3.1, gene deletion on homozygous and heterozygous mouse cochleas in adulthood and aging. *Hearing Research* 134:71-76; Van der Wees, J., Van Looij, M. A., de Ruiter, M M, Elias, H., van der Burg, H., Liem, S. S., Kurek, D., Engle, J. D., Karis, A., van Zanten, B. G., de Zeeuw, C. I., Grosveld, F. G., van Doornick, J. H. (2004) Hearing loss following Gata3 haploinsufficiency is caused by cochlear disorder. *Neurobiol Dis* 16:169-78; Dabdoub, A., Puligilla, C., Jones, J. M., Fritzsch, B., Cheah, K. S., Pevney, L. H. Kelley, M. W. (2008) Sox2 signaling in prosensory domain specification and subsequent hair cell differentiation in the developing cochlea. *Proc Natl Acad Sci USA* 105:18396-401; and Appler, J., Koundakjian, E., Lu, C, Goodrich, L. (2009) Gata3 regulates neurite extension and targeting of spiral ganglion neurons. *Proc, 7th Molecular Biology of Hearing and Deafness conference.* June 20-23, Harvard Medical School, Boston, Mass., USA).

The Adenovirus-mediated transduction of the transcription factor atonal homologue 1 (Atoh1, also known as Math1, ATH1, HATH1 or bHLHa14) (NCBI accession No. BC069578 version GI:47480322 (HGNC:797), Uniprot accession Nos. Q92858; Q14CT9) into mouse or guinea pig cochlear cells has been described to lead to the generation of a cochlear hair cell-like phenotype from supporting cells, which led to secretion of trophic factors, the attraction of neurite outgrowth and the formation of functional synapses between the transformed cells and auditory spiral ganglion cells. Accordingly, the methods described herein contemplate the transfection of the transcription factor atonal homologue 1 into cochlear cells using electroporation, without the need for viral vector-mediated delivery.

Other transcription factors which modulate the expression of neurotrophic factors in cells are known in the art. For example, the transcription factor SRY-box-containing gene 10 (Sox10) induces a greater than 100 fold up regulation of the expression of ciliary neurotrophic factor in Schwann cells in the mouse, whilst knockdown of Sox10 results in a reduction of expression ciliary neurotrophic factor by more than 80%. Accordingly, the methods described herein contemplate the transfection of cochlear cells by electroporation of a nucleic acid molecule encoding a transcription factor, wherein the transcription factor modulates the expression of an endogenous neurotrophic factor for spiral ganglion cell neurons, or wherein the transcription factor modulates the expression of an exogenous polynucleotide sequence which encodes a neurotrophic factor for spiral ganglion cells and which is transfected with the transcription factor.

The up regulation of a gene sequence may be achieved by the use of gene targeting constructs to generate transcription units formed by homologous recombination between an endogenous target gene and the targeting construct. In such methods, expression of a desired targeted gene in a cell (i.e., a desired endogenous cellular gene) is altered by the introduction by homologous recombination into the cellular genome at a preselected site, of DNA which includes at least a regulatory sequence, an exon and a splice donor site. These components are introduced into the chromosomal (genomic) DNA in such a manner that this, in effect, results in production of a new transcription unit (in which the regulatory sequence, the exon and the splice donor site present in the DNA construct are operatively linked to the endogenous gene). As a result of introduction of these components into the chromosomal DNA, the expression of the desired endogenous gene is altered.

The production and use of targeting constructs are described, for example, in U.S. Pat. No. 5,641,670 (Treco et al.), the entire contents of which are incorporated herein by reference. Endogenous genes which may be up regulated by these techniques include neurotrophic factor genes selected from Neurotrophin-3 (NT-3) or Neurotrophin-3 precursor molecule or a preprotein form thereof (NCBI Accession No. HGNC:8023, Swiss Prot Accession Number P20783) or homologs or human variants thereof; Neurotrophin 4/5 (NT-4/5, NT-4, NT-5, NTF4, NTF5) or a preprotein form thereof ((HGNC:8024). Ensembl accession No. ENSP00000328738, GenBank accession No. AAA60154, version GI:190265) or homologs or human variants thereof; Nerve growth factor (NGF) (NCBI Accession No. NP_002497.2 version GI:70995319) (HGNC:7808), Ensembl accession no. ENSP00000358525), preprotein forms thereof or homologs or human variants thereof; Brain derived neurotrophic factor (BDNF, Brain-derived neurotrophic factor Precursor, Abrineurin) (the preprotein form of which is described in NCBI Accession No. NP_001137277.1 version GI:219842288, UniProtKB/Swiss-Prot Accession No. P23560) or homologs or human variants thereof; glial cell line-derived neurotrophic factor (GDNF, glial cell derived neurotrophic factor precursor)

(NCBI Accession No. HGNC:4232 (gene) or the preprotein forms as described in NCBI Accession Numbers NP_000505 and NP_000505.1) or homologs or human variants thereof; ciliary neurotrophic factor (CNTF) (NCBI Accession No. NP_000605 version GI:4758020 (HGNC: 2169), UniProtKB/Swiss-Prot Accession No. P26441) or homologs or human variants thereof; Activity dependent neurotrophic factor (ADNF, ADNP1; KIAA0784; ADNP, or Activity-dependent neuroprotector homeobox protein) (Ensembl Accession Numbers: ENSP00000360662, ENSP00000379346, ENSP00000342905, and ENSP00000379349) or homologs or human variants thereof, or fragments thereof, or the ADNF homologues ADNF-9 or the active peptide region with an amino acid sequence of SALLRSIPA, or ADNF-14 (neuropeptide) or the neuroprotective NAP peptide of ADNF with an amino acid sequence of NAPVSIPQ; the cytokine trophic factor leukaemia inhibitory factor (LIF) (NCBI accession No. HGNC:6596 (genomic sequence), UniProtKB/Swiss-Prot Accession No. NP_002300.1 version GI:4504991 (polypeptide), typically in conjunction with a neurotrophin such as NT-3; and Fibroblast growth factor (FGF 1, FGF 2) (NCBI accession No NM_002006 (genomic sequence), UniProtKB/Swiss-Prot Accession No. P09038 (polypeptide)) or homologs or human variants thereof, which is believed to interact with NT3 and to support neurite outgrowth and growth cone development, or in a combination of FGF-2 & GDNF; Apyrase; or ectonucleoside triphosphate diphosphohydrolase 2 (ENTPD2) (NCBI Accession no. NM 001246); a gene encoding a polypeptide involved in the melanocortin signalling pathway, for example alpha-melanocyte stimulating hormone (alpha-MSH), proopiomelanocortin (POMC) (HGNC Accession No. HGNC:9201), or a gene encoding a morphogen, for example a bone morphogenetic protein (BMP), Sonic hedgehog, or Wingless/Wnts, a gene encoding an axon guidance factor, such as laminin, Netrin-1, an Ephrin, a semaphorin, a Slit such as a 3 slit homolog, slit2 or slit3 or a cytokine such as Leukaemia inhibitory factor.

The modulation of expression of the endogenous gene may be the down regulation of expression of an endogenous gene. The down regulation of expression of the endogenous gene may, for example, be the down regulation of a transcription factor which constitutively or inducibly inhibits the expression of a neurotrophic factor by a cochlear cell, such as a cochlear mesenchymal cell, which results in the mesenchymal cell expressing a neurotrophic factor.

The down regulation of an endogenous gene may utilize the targeted disruption of the expression of one or more endogenous genes using any nucleic acid molecules which selectively target and inhibit the expression of the genes, such as antisense sequences, varieties of small interfering RNA (siRNA) sequences, shRNA sequences, ribozyme sequences and the like. The "expression" of endogenous genes is intended to encompass the transcription and/or translation of endogenous gene sequences.

Methods for the design, synthesis, and delivery of antisense nucleic acid molecules are well known in the art. The antisense molecules may be DNA or RNA, or partial or complete synthetic analogues thereof. Antisense polynucleotides of the invention may be generated which are at least substantially complementary along their length to the region of the gene in question. Binding of an antisense polynucleotide to its complementary cellular sequence may interfere with transcription, RNA processing, transport, translation and/or mRNA stability.

Suitable antisense oligonucleotides may be prepared by methods well known to those of skill in the art. Typically antisense oligonucleotides will be synthesized on automated synthesizers. Suitable antisense oligonucleotides may include modifications designed to improve their delivery into cells, their stability once inside a cell, and/or their binding to the appropriate target. For example, the antisense oligonucleotide may be modified by the addition of one or more phosphorothioate linkages, or the inclusion of one or more morpholine rings into the backbone. The antisense oligonucleotide may be 10-30 base pairs in length.

As a practical matter, whether any particular nucleic acid molecule is no more than 90% identical to, for instance, the nucleotide sequence of other known gene or mRNA or cDNA sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman to find the best segment of homology between two sequences (Advances in Applied Mathematics 2:482-489 (1981)). When using Bestfit or any other sequence alignment program to determine whether a particular sequence is, for instance, 90% identical to a reference sequence, the parameters are set such that the percentage of identity is calculated over the full length of the reference nucleotide sequence and that gaps in homology of up to 5% of the total number of nucleotides in the reference sequence are allowed. A preferred method for determining the best overall match between a query sequence and a subject sequence, also referred to as a global sequence alignment, can be determined using the FASTDB computer program based on the algorithm of Brutlag and colleagues (Comp. App. Biosci. 6:237-245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. Only bases outside the 5' and 3' bases of the subject sequence, as displayed by the FASTDB alignment, which are not matched/aligned with the query sequence, are calculated for the purposes of manually adjusting the percent identity score.

Small interfering RNA (siRNA) sequences are small, usually double-stranded RNA oligonucleotides, for example at 19, 21, 27 or 29 bases in length, with or without overhangs, which specifically hybridize with RNA sequences of interest and which serve as substrates for the RNA-induced silencing complex. Double-stranded RNA molecules may be synthesized in which one strand is identical to a specific region of the mRNA transcript to be silenced, and this double stranded RNA may be introduced directly. Alternatively, corresponding dsDNA can be employed, which, once presented intracellularly is converted into dsRNA. Methods for the design and synthesis of suitable siRNA molecules for use in RNA interference (RNAi) and for achieving post-transcriptional gene silencing are well known to those of skill in the art. For example, rules for the rational design of siRNA are available online in "Rules of siRNA design for RNA interference (RNAi)" at protocol-online.org/prot/Protocols/Rules-of-siRNA-design-for-RNA-interference--RNAi--3210.html. These rational design principals are also described in Elbashir S M et al. (2001) Duplexes of 21-nucleotide RNAs mediate RNA interference in cultured mammalian cells. Nature. 411:494-498; Elbahir S M et al. (2001). Functional anatomy of siRNAs for mediating efficient RNAi in *Drosophila melanogaster* embryo lysate. EMBO J. 20:6877-6888; Elbashir S M et al. (2002). Analysis of gene function in somatic mammalian cells using small interfering RNAs. Methods. 26:199-213; Reynolds A, Leake D, Boese Q, Scaringe S, Marshall W S, Khvorova A. Rational siRNA design for RNA interference. Nat Biotechnol. 2004 March; 22(3):326-30; and online at basic.northwestern.edu/biotools/oligocalc.html. The entire contents of each of these publications is incorporated herein by reference.

Examples of two siRNA design tools which implement the rational siRNA principals discussed above are design algorithms offered by Dharmacon, Inc a downloadable Microsoft Excel™ template, written by Maurice Ho at boz094.ust.hk/RNAi/siRNA.

The skilled addressee will appreciate that a range of suitable siRNA or nucleic acid molecules comprising an siRNA sequence which is capable of inhibiting the expression of an endogenous gene can be identified and generated based on knowledge of the sequence of the genes in question using routine procedures known to those skilled in the art without undue experimentation. Those skilled in the art will appreciate that there need not necessarily be 100% nucleotide sequence match between the target sequence and the siRNA sequence. The capacity for mismatch is dependent largely on the location of the mismatch within the sequences. In some instances, mismatches of 2 or 3 nucleotides may be acceptable but in other instances a single nucleotide mismatch is enough to negate the effectiveness of the siRNA. The suitability of a particular siRNA molecule may be determined using routine procedures known to those skilled in the art without undue experimentation.

Although the maximal effects of antisense nucleic acids and siRNA on the specific inhibition of RNA or protein expression are comparable, siRNA generally produces a longer-lasting effect. Although siRNAs may be introduced into a cell by way of a vector, for example via a viral-mediated delivery mechanism such as an adeno-associated virus vector, in the context of the present invention the siRNA will be delivered exogenously by electroporation. Techniques for the administration of siRNA sequences locally or systemically to mice (Yano et al, (2004) *Clinical Cancer Research* 10: 7721-7726), to primates (Zimmermann et al, (2006) *Nature* 441(7089):111-114) and to humans (Nogawa et al. (2006) *J Clin Invest* 115:978-985) have been described, and these have demonstrated that this class of molecules can be used to reduce the expression of target genes in vivo. The entire contents of each of these citations is incorporated herein by reference.

Ribozymes, such as hammerhead or hairpin ribozymes, are capable of the targeted catalytic cleavage and splicing of specific RNA sequences, including mRNA and genomic RNA sequences. The design and methods for the delivery of ribozymes are reviewed, for example, in Vaish, Kore and Eckstein (1998) *Nucleic Acids Research* 26:5237-5242; in Lieber and Strauss (1995) *Mol. Cell. Biol.* 15:540-551; and in Usman and Blatt (2000) *J Clin Invest* 106:1197-1202, the entire contents of each of which are incorporated herein by reference.

Short hairpin RNA (shRNA) is a sequence of RNA with a tight hairpin turn structure which is introduced into cells as part of a vector which comprises a constitutive promoter such as a U6 promoter to allow shRNA to be constitutively expressed. The shRNA hairpin structure is cleaved by the cellular machinery into siRNA, which is then bound to the RNA-induced silencing complex (RISC). This complex binds to and cleaves mRNAs which match the siRNA that is bound to it. The vector comprising the shRNA sequence is usually passed on to daughter cells in cell division, allowing the gene silencing to be inherited. Strategies for designing shRNA sequences and nucleic acid molecules comprising shRNA for use in mammalian cells are known, for example McIntyre and Fanning, Design and cloning strategies for constructing shRNA expression vectors, *BMC Biotechnol.* (2006) 6:1.

The nucleic acid may be microRNA. The term microRNA or "miRNA" as used herein has the ordinary and plain meaning of a non-coding RNA molecule found in eukaryotes which is involved in RNA-based gene regulation. The term can be used to refer to the single-stranded RNA molecule processed from a precursor or in certain instances the precursor itself or a mimetic or inhibitor thereof. The involvement of microRNA in normal cochlear function and in a familial cochlear disorder has been described in Mencía et al., *Nature Genetics* (2009) 41(5):609-613. It is anticipated that the modulation of microRNA activity in cells of the cochlea, either by the introduction of microRNA or microRNA mimics into cells or the silencing of endogenous microRNA with a microRNA inhibitor may provide an approach for modulating the expression of particular targeted genes. Strategies for the administration of microRNA into cells or tissues of subjects have been described in International patent publication No. WO 2008/073920, which describes methods of modulating gene expression, or biologic or physiologic pathways in a cell, a tissue, or a subject comprising administering to the cell, tissue, or subject an amount of an isolated nucleic acid or mimetic thereof comprising a specific microRNA or microRNA inhibitor nucleic acid sequence in an amount sufficient to modulate the expression of a gene positively or negatively modulated by the microRNA. Studies have demonstrated therapeutic application of modulating microRNA in animals, including primates.

Techniques for the design of microRNA and microRNA inhibitors are readily available. A database of known microRNA sequences, new microRNA sequences and predicted microRNA targets is maintained at miRBase microrna.sanger.ac.uk and described in "miRBase: tools for microRNA genomics" Griffiths-Jones S, Saini H K, van Dongen S, Enright A J. NAR 2008 36(Database Issue): D154-D158; "miRBase: microRNA sequences, targets and gene nomenclature" Griffiths-Jones S, Grocock R J, van Dongen S, Bateman A, Enright A J. NAR 2006 34(Database Issue):D140-D144; and "The microRNA Registry." Griffiths-Jones S. NAR 2004 32(Database Issue):D109-D111.

Commercial services are available for the design and synthesis of specific microRNA inhibitors based on a provided target sequence.

In general, each of these classes of molecules appears to be well tolerated, either when administered to human or animal subjects systemically, such as via intravenous routes, as a bolus or by sustained release techniques subcutaneously, or when directly applied to cells.

Agents Other than Nucleic Acid Molecules

Also contemplated in the methods described herein is the electroporation of small neuroprotective polypeptides which may support the survival of cochlear hair cells and/or spiral ganglion cells. Examples of such molecules include the neuroprotective NAP peptide, activity dependent neurotrophic factor, FNK peptide. $ACTH_{4-9}$ analogue Org 2766, or molecules comprising these peptides which retain neuroprotective activity in the cochlea.

Electroporation

The methods described herein use electroporation to deliver the agent into the cytoplasm and/or nucleus of cochlear cells which lie close to the electrode of the cochlear implant.

The use of non-invasive electroporation to successfully deliver a nucleic acid molecule to cells of an intact non-cochlear tissue has been previously described, for example, in U.S. Pat. No. 6,972,013 (Zhang and Rabussay), the entire contents of which is incorporated herein by reference.

As used herein, the term "transfection" refers to the transfer of an agent, including but not limited to a nucleic acid molecule, into the cytoplasm and/or nucleus of a cell by electroporation. In certain embodiments in which the agent is a nucleic acid molecule, the nucleic acid molecule encodes a polypeptide product which is expressed by the cell. In certain embodiments in which the agent is a nucleic acid molecule, the nucleic acid molecule acts upon the transcription and translation machinery of the cell. A transfected cell may carry the nucleic acid molecule product permanently if the nucleic acid molecule agent is stably incorporated into the cell's genome. A transfected cell may carry the nucleic acid molecule product transiently if the nucleic acid molecule agent is not incorporated into the cell's genome.

The agent may be delivered to the cochlea at the time the electroporation electrode is inserted into the cochlea, or before the insertion of the electroporation electrode or after the insertion of the electroporation electrode. The agent may be provided in a diffusible form, such as incorporated in or associated with a biodegradable or biocompatible viscous liquid or gel solution surrounding the electrode array of the cochlear implant. The viscous liquid or gel solution may comprise polyacrylic acid (PAA), polyvinyl alcohol (PVA), polylactic acid (PLA) and/or polyglycolic acid (PGA). Pluronic F127 (BASF) at <30% solution may also be used to stabilise the media containing the agent. This approach may provide an advantage in that the agent is presented to the target cochlear cells with the electrode array in situ in a stable concentration at the time of electroporation.

Where the agent comprises a nucleic acid molecule the agent may be presented in a diluent solution which comprises ions and proteins or the agent may be diluted in sterile distilled deionised water, provided that the diluent solution does not substantially adversely affect the efficiency of electroporation. Typically water is used as the diluent, with the nucleic acid molecule provided typically at a concentration of from 10 ng/µl to 1 µg/µl. The nucleic acid molecule may be provided within a buffered solution, such as phosphate-buffered saline (PBS; e.g. pH 7.4), or a perilymph-like solution (for example as described by Salt, A. N. Konishi, T. (1986) The cochlear fluids: Perilymph and endolymph. Eds. Altschuler, R. A., Hoffman, D. W., Bobbin, R. P. In: *Neurobiology of Hearing: The Cochlea*. New York, Raven Press, pp. 109-122), and may be in the presence of divalent cation chelators such as ethylenediaminetetraacetic acid (EDTA) for stabilization of the molecules.

Typically the solution comprising agent is delivered in the vicinity of the apex of the cochlea, so that the solution comprising the agent flows back down the cochlea chamber and displaces the media lying within the cochlea chamber. The volume of the human scala tympani is in the order of 30 µl, the scala vestibuli 22 µl, and the scala media 2 µl. In order to ensure that the chamber contains sufficient agent the nominal volume of solution comprising the agent to be delivered to the cochlea may be in the order of 30 µl. Typically, the controlled delivery of such a volume may be achieved through the use of a mechanical infusion micropump, a microsyringe, or a mini-osmotic pump (Alza Corporation, Palo Alto, Calif., USA). Once the agent and electrode are present within the appropriate chamber(s) electroporation takes place, and in certain embodiments the electroporation electrode is then removed. In these embodiments of the invention the electroporation electrode may be withdrawn from the cochlea as a separate action to the placement of the cochlear implant, and typically the electrode is removed before the insertion of the cochlear implant.

Electrodes for use in the electroporation methods described herein deliver the electric field which is required for electroporation to the cochlear tissue. Typically the electrodes will comprise electrically conductive, non-toxic or bio-inert metal, for instance platinum, gold, tungsten, or stainless steel. The electroporation electrode may be electrically conductive at its surface along the entire length of the electrode inserted into the cochlea. The electroporation electrode may be electrically conductive at its surface along one or more portions of the entire length of the electrode inserted into the cochlea, and electrically non-conductive at its surface along other portions of its length. The non-conductive portions may be insulated at the surface of the electrode with a coating, such as a resin or plastic coating. The non-conductive portions may be made of a non-conducting material, such as a resin or plastic.

In certain embodiments the electrodes may be inserted and removed from the cochlea independently of the cochlear implant, for example where the electroporation electrodes are not part of the cochlear implant. In these embodiments, at least one electrode which is used for electroporation is typically inserted into and along one or more of the scala tympani or the scala vestibuli of the cochlea before or after the agent is introduced into the same chamber(s) of the cochlea.

In other embodiments at least one of the electroporation electrodes is provided as part of the cochlear implant.

The electroporation electrode may comprise a lumen, channel or groove which carries the agent and allows the delivery of the agent to the chamber(s) of the cochlea, or it may be associated with a separate catheter or cannula, such as a silicon or polymer tube which is attached to the electrode. Alternatively, the agent may be introduced into the cochlea via a cannula which may be inserted or removed independently to the electroporation electrode.

In certain embodiments of the methods described herein, at least one electrode which is used for electroporation is provided by the cochlear implant. The term "cochlear implant" or "cochlear implant device" as used herein refers to a device which is at least partially implanted in the scala tympani or the scala vestibuli of the cochlea for the purpose of restoring hearing by direct electrical stimulation of the cochlear nerve. A cochlear implant is commonly termed a "bionic ear". Examples of cochlear implants and/or electrodes for cochlear implants are described in U.S. Pat. No. 7,451,000 (Cochlear Limited), U.S. Pat. No. 7,406,352 (Cochlear Limited); U.S. Pat. No. 7,367,992 (Cochlear Limited), U.S. Pat. No. 7,349,744 (Cochlear Limited); U.S. Pat. No. 7,346,397 (Cochlear Limited), U.S. Pat. No. 7,340,308 (Advanced Cochlear Systems, Inc.), U.S. Pat. No. 7,319,906 (Advanced Bionics Corporation), U.S. Pat. No. 7,317,944 (Advanced Bionics Corporation), and U.S. Pat. No. 7,315,763 (Advanced Bionics Corporation), the entire contents of each of which is incorporated by reference.

A cochlear implant possesses at least one electrode and more typically a series of independently addressable "nodes" along the length of the region of the implant lying within the cochlea, with each node electrically insulated from other nodes. During the normal operation of the cochlear implant, the nodes receive stimuli originating from an external control unit and provide an electrical stimulus to the spiral ganglion cells by creating a voltage between the nodes in a bimodal fashion to prevent polarization of the nodes.

For the electroporation methods described herein, in certain embodiments some or all of the nodes of the cochlear implant may act as a single electrode. In other embodiments, individual nodes or groups of nodes may act as an electrode and other individual nodes or groups of nodes act as a second electrode. In certain embodiments the cochlear implant may provide a plurality of electrodes and second electrodes. Examples of configurations of nodes and/or dedicated electroporation electrodes on a cochlear implant are illustrated in FIG. 5.

Figure 5A:
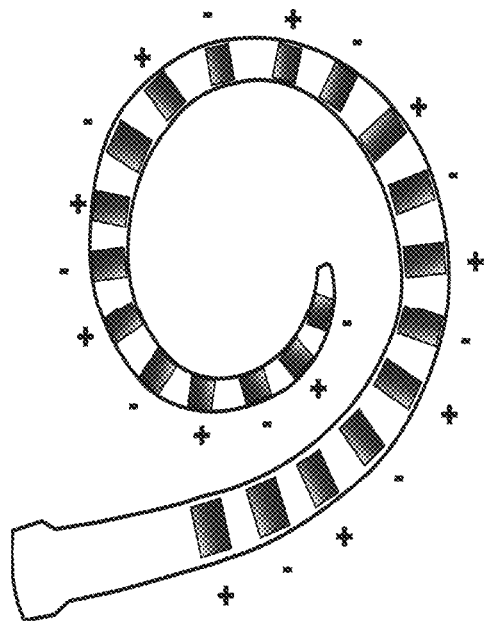
FIGS. 5A-E provide a series of diagrams which illustrate possible cochlear implant electrode "node" configurations which may be suitable for electroporation. The positions of nodes of the cochlear implant electrode are set out as grey-shaded boxes along the length of the electrode, which is shaped to fit the scala tympani of the cochlea.
Figure 5B:
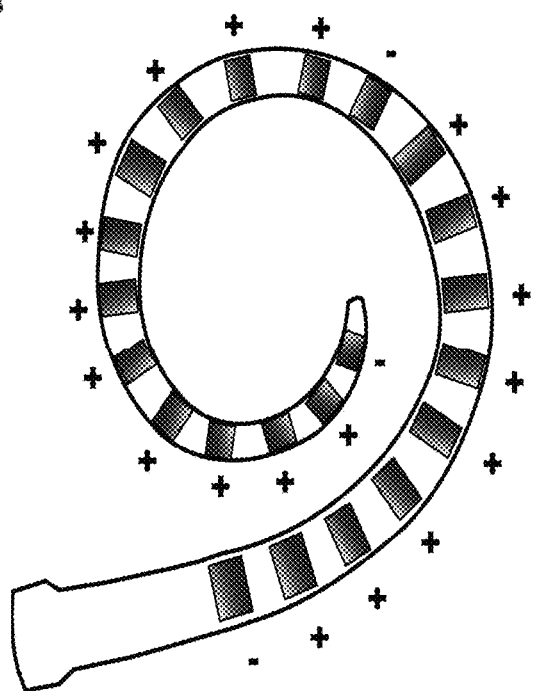
Figure 5C:
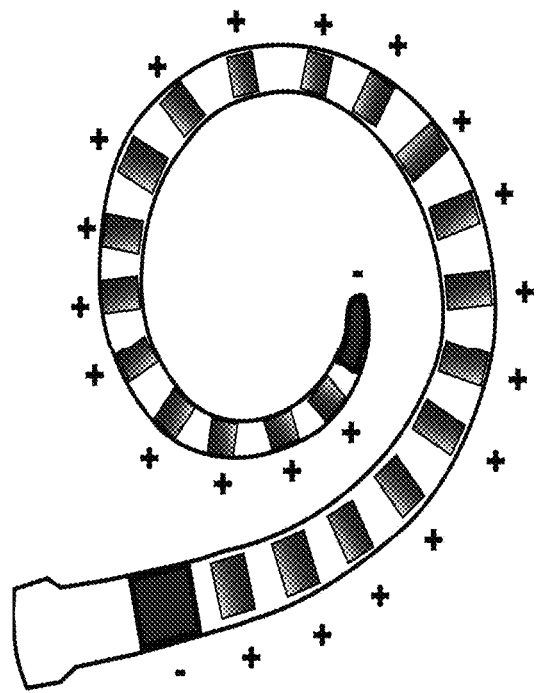
Figure 5D:
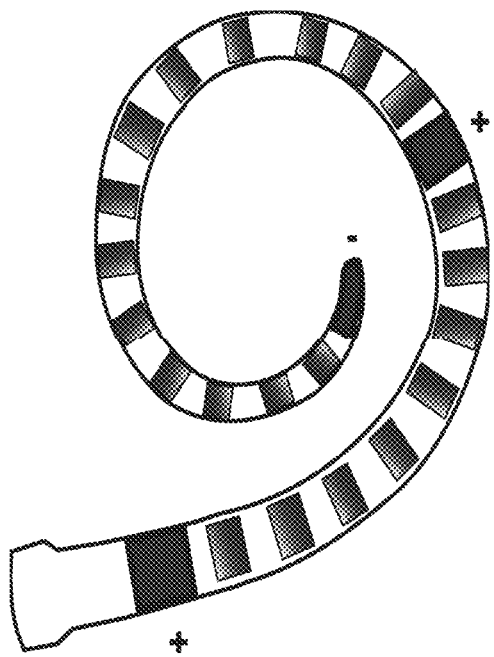
Figure 5E:
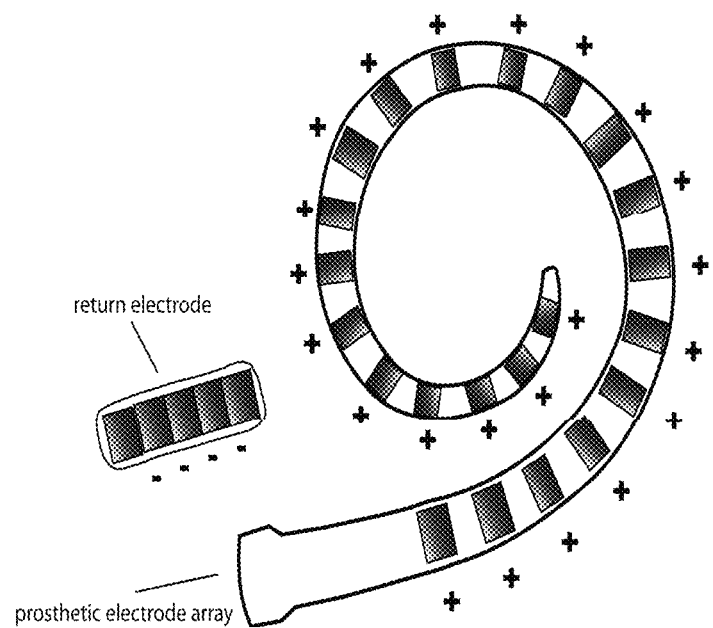

For the purposes of electroporation a cathode and an anode is required. When using a cochlear implant all the nodes, or specific nodes along the implant, may be used to generate a transient dialectric breakdown of the lipid bilayer of the plasma membrane of the target cells. In one embodiment, this may be performed by simultaneously polarizing some or all of the nodes relative to at least one second electrode which is located distant to the cochlear implant, for example outside of the cochlea, to provide a current return path. An example of such a configuration is illustrated in FIG. 5E. For example, an external electrode may be located in the fascia tissue which lies along the temporal bone of the subject. This second electrode is typically the cathode (negative) terminal relative to the nodes of the electrode array. In this unipolar delivery mode, the electrical voltage used to electroporate cochlear cells is typically provided within a voltage range of from 1 to 100 volts, more typically within a voltage range of from 10 to 20 volts.

In another embodiment electroporation utilises bimodal current delivery in which at least one and more typically several nodes of the implant are configured as anodes, and with one or more other nodes interspersed along the electrode array of the cochlear implant configured as cathode second electrodes for current delivery. Examples of such embodiments are illustrated in FIGS. 5A and 5B. In this configuration, the polarity of individual nodes may be altered over time during electroporation to ensure an even transfection of target cells along the length of the array, and to minimise toxic effects which may arise at either the cathode or anode. Using a bimodal approach, the voltage required for electroporation may be reduced because of the high field strength between the closely associated nodes of the electrode.

In certain embodiments the current for electroporation is provided by dedicated circuitry in the cochlear implant. In these embodiments the dedicated circuitry generates the required electrical pulse profile in an electroporation mode for use during the implantation procedure and at later stages if additional gene transfection is performed. The implant stimulator may then be switched to a conventional stimulus mode for operation as a cochlear prosthesis/auditory nerve stimulator.

In certain embodiments, cochlear implants are provided in which one or more dedicated electroporation electrode "nodes" are built into the implant for the purpose of providing the electroporation stimulus to the cochlear tissue. These dedicated nodes may be driven via an external isolated electroporation-driving circuit, or the one or more dedicated electroporation electrode nodes could be driven externally by electroporation circuitry. In certain embodiments the dedicated electroporation electrode nodes are not used in the normal operation of the cochlear prosthesis in providing direct electrical stimulus to the spiral ganglion cells as a result of auditory stimulation. Examples of such embodiments are illustrated in FIGS. 5C and 5D.

Figure 6:
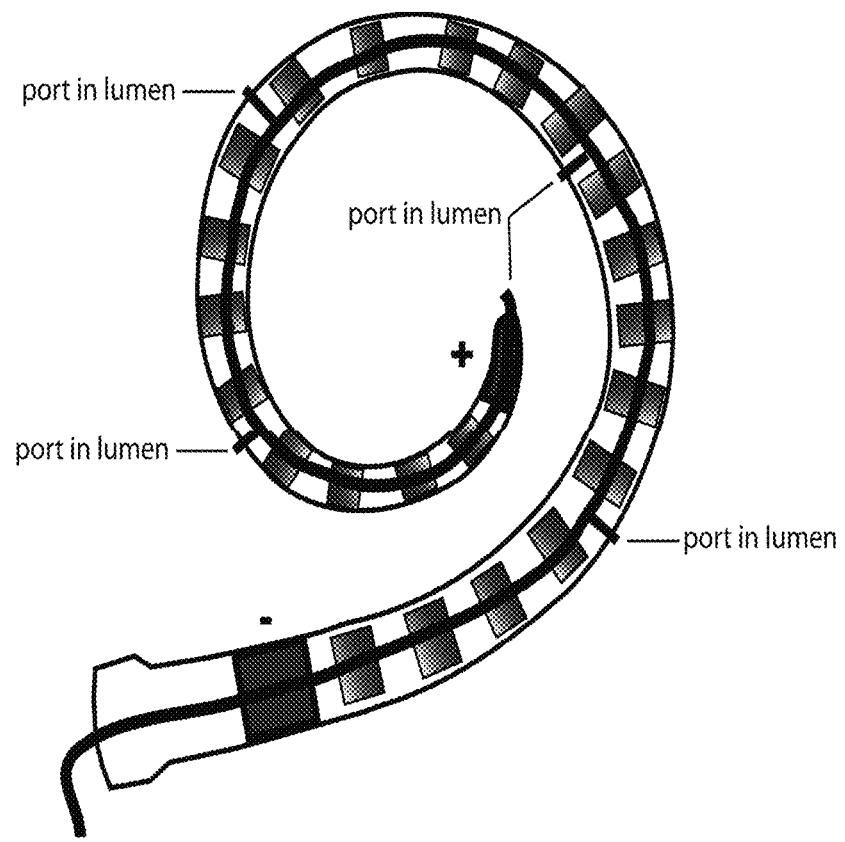
FIG. 6 provides a diagram illustrating one possible configuration of a cochlear implant for delivery of the agent to sites within the cochlea as well as the delivery of an electroporation current. In this embodiment the cochlear implant comprises the "distal current return" electrode configuration for electroporation and an integrated catheter for agent delivery into the cochlear fluid compartment prior to electroporation. In this embodiment the black electrodes are specifically dedicated for electroporation mode only and are sufficient for efficient gene delivery. The solid black line is symbolic of an internal lumen, such as a catheter, which lies within the cochlear implant and which allows delivery of the therapeutic molecule to one or more sites within the cochlea in situ, prior to electroporation of the cochlear tissue.

In embodiments in which the cochlear implant provides at least one electroporation electrode, the agent may be provided via a lumen, channel or groove in the cochlear implant. These forms of electrode may allow multiple rounds of introduction of agent into the cochlea following implantation of the cochlear implant and therefor multiple rounds of electroporation. An example of such an embodiment is illustrated in FIG. 6. The use of a cochlear implant with a lumen to deliver agents to the cochlea is described, for example, in Paasche et al., (2003) *Otology & Neurology* 24:222-227, the entire contents of which is incorporated herein by reference.

The lumen of the cochlear implant may be sealed following delivery of the agent.

U.S. patent application publication No. 2008/0214986, the entire content of which is incorporated herein by reference, describes the use of gel compositions with a predetermined conductivity for use in optimising the electroporation of tissues. In certain embodiments, the electrodes and or cochlear implant may be coated with gel, as described in this publication, to provide a degree of control over the conductivity of the volume surrounding the electrodes.

In certain embodiments of the methods described herein the the cochlear implant comprises at least one electrode which is used for electroporation, and the agent is delivered to the desired chamber of the cochlea using a catheter or cannula which is not associated with the cochlea implant. In these embodiments typically the catheter or cannula is inserted into the appropriate chamber(s) of the cochlea and the solution comprising the agent is delivered. The catheter or cannula is then withdrawn, the cochlear implant is introduced and electroporation takes place, as described above.

The electroporation stimulus is typically provided in a square wave configuration of from 100 µs to 500 ms pulse duration, more typically in a 30 ms pulse width being commonly used. Multiple pulses are commonly used, with typically from 25 to 200 pulses, more typically from 50 to 100 pulses, with an interval between each pulse of 1, 2, 3, 4, 5, 6, 7, 8, 9, or 10 seconds. Ramped waveforms may also be used, as these may provide a faster onset of electroporation dialectric breakdown of the cell membrane for agent delivery, while minimizing current delivery. As such stimuli delivered to the intact cochlea of a subject may be perceived by the subject as excessively loud noise, typically the subject will be under general anaesthetic during electroporation.

The delivery of the electroporation current during the electroporation procedure for delivery of an agent may typically last from 5 to 10 minutes, depending upon the number of pulses and the delay between pulses.

EXAMPLES

Example 1

Electroporation Transfection of Cochlear Mesenchymal Cells In Situ

Experiments were carried out to determine whether pulsed electrical fields of a specific profile, delivered via electrodes placed in the cochlea of a guinea-pig, could provide localized transfection of specific gene constructs in the mesenchymal cells lining the cochlear scala tympani. One of two different naked cDNA gene constructs were introduced into each cochlea. The cDNA gene constructs utilized commercial bicistronic expression vectors where fluorescence reporter proteins and therapeutic molecules were jointly expressed via an IRES (internal ribosome entry site) element, and expression was driven by the cytomegalovirus promoter (CMVp).

The two cDNA constructs were:
1. CMVp-TRPC3-IRES-DsRed2
    a. The plasmid (pIRES2-DsRed2 (Clontech™), including the IRES bicystronic expression element and the DsRed2 fluroescence reporter.
    b. The TRPC3 gene (Accession no. AB090949.1) element was cloned from the guinea-pig (*Cavia parcellus*) by PCR. The complete open reading frame was subcloned into the vector upstream of the IRES element.
2. CMVp-BDNF-FLAGtag-IRES-eGFPn
    a. The plasmid backbone utilized the pShuttle-IRES-hrGFP-1 vector (Strategene™)
    b. The BDNF construct (Accession No. HM_183060) was ligated into the multicloning site 5' to the 3× FLAG-tag and IRES elements. The eGFPn reporter was downstream of the IRES.

Cochleae from guinea-pig temporal bones were placed in a humidity chamber with Dulbecco's phosphate buffered saline (PBS). The vectors were injected into the scala tympani compartment of the guinea pig cochlea using a polyethelene cannula (10 µl; 0.1 to 1.0 µg/ml, dissolved in distilled water), after perforation of the round window at the base of the cochlea, scala media compartment, and placement of a fenestration at the apex of the cochlea to permit perfusion of the scala tympani compartment.

After perfusion of the scala media with the cDNA gene construct, a shaped silver wire electrode, modelling a cochlear implant prosthesis, was inserted through the round window membrane perforation, into the basal turn region of scala tympani (see FIG. 1). This approach is a useful model of a cochlear implant, and has in the past been used in early translational research into electrical stimulation of the auditory nerve, directed toward providing a prosthesis for restoring hearing function utilising unipolar electrodes inserted into the cochlea, including access via the round window or through the base of the cochlea to directly stimulate the auditory nerve. In these early studies current return was provided by a second electrode located at either the base or apex of the cochlea or in adjacent tissue, as for the current study. In the present study, a second electrode, inserted into either the apex of the cochlea, or into the oval window (basal turn scala vestibuli), completed the current return pathway. The basal electrode typically acted as an anode pole, with the second electrode acting as the current source (cathode). In some experiments the polarity was reversed.

A range of electroporation profiles were utilized in these experiments, as set out in Table 1, using an isolated stimulator (Grass Instruments, USA), gated to produce square wave voltage-steps via a computer interface (Labview). Controls included addition of the cDNA gene constructs with and without a liposomal transfection reagent (lipofectamine 2000; Invitrogen) transfection media and insertion of the electrodes, but no voltage delivery.

After electroporation, the cochleae were maintained in PBS for 30 minutes at room temperature and then the tissues were dissected and placed into organotypic culture (37° C., 5% $CO_2$) in 24 well tissue culture plates. The culture media included Dulbecco's modified Eagle medium (DMEM; Gibco), 10% fetal bovine serum (FBS; Gibco), 25 mM Hepes (Sigma-Aldrich); 6 mg/ml glucose & 300 units/ml penicillin (Sigma-Aldrich).

The tissue was imaged by removing the tissue from the culture wells between 24 h and 96 h, after which the tissue was placed in culture medium on a coverslip for epifluorescence imaging (Leica, German; Andor emCCD, Ireland). Cells expressing the CMVp-TRPC3-IRES-DsRed2 gene construct were detected by expression of the DsRed2 signal in cytoplasm using a red emission filter (N2.1; Leica, Germany). Expression of the CMVp-BDNF-FLAG tag-IRES-eGFPn construct was detected using a green emission filter (GFP, Leica, Germany) for the nuclear GFP signal. Expression of the therapeutic BDNF molecule by the target cells in the cochlea was confirmed by detection of the FLAG-tag, using an anti-FLAG antibody (Sigma, cat. F7425), detected via a secondary antibody (goat-anti-rabbit IgG; FITC). Expression of BDNF was confirmed using confocal imaging (Zeiss 710 LSM. Germany).

The results which were obtained are summarized in Table 1. A total of 14 experiments were performed to assess the potential for electroporation-based gene delivery in the adult guinea-pig cochlea. Gene construct CMVp-TRPC3-IRES-DsRed2 was delivered to 8 cochleae. Two of these experiments were controls in which electroporation was omitted. In an additional two control experiments, no cDNA was delivered to the cochlea, but the tissue was placed into organotypic culture to confirm autofluorescence levels and check for possible vector carry-over. The control experiments did not exhibit expression of the reporter gene.

Figure 2:
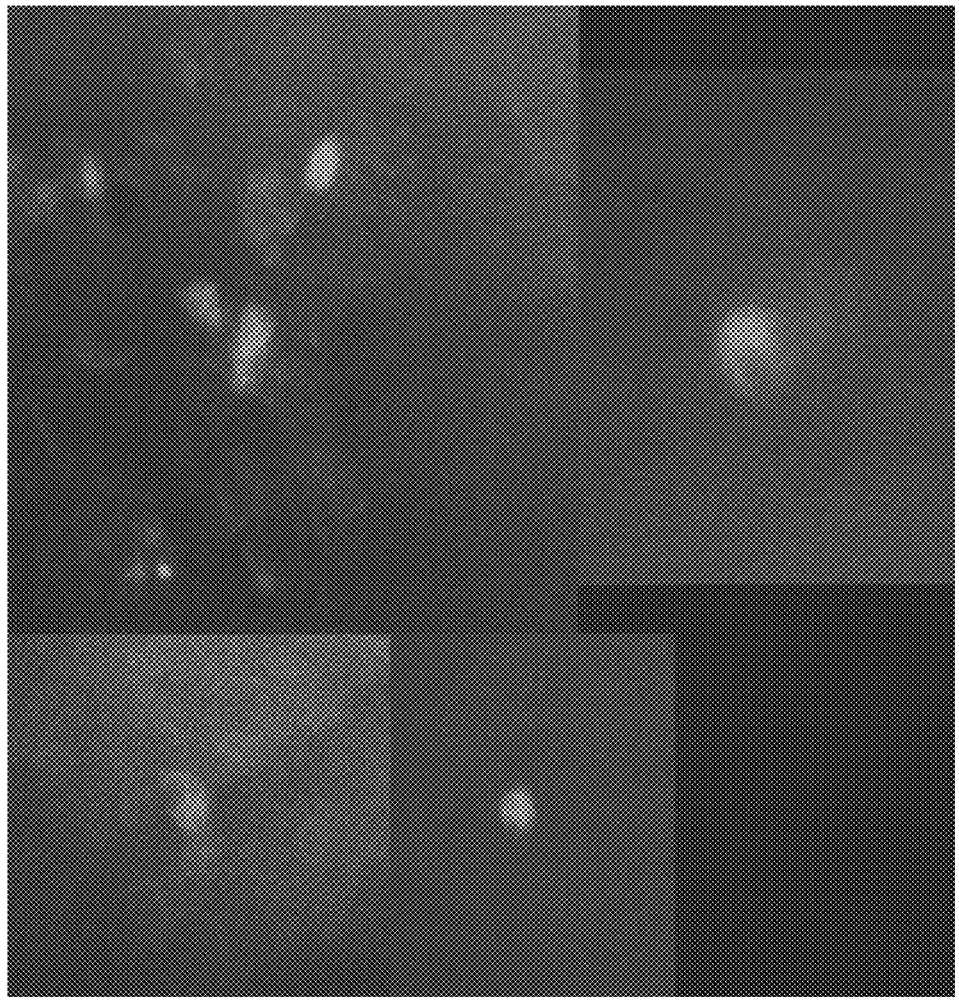
FIG. 2 shows a group of photomicrographs illustrating the successful electroporation of guinea-pig cochlea mesenchymal cells using the method of Example 1. The expression of DsRed2 reporter is evident in cochlear mesenchymal cells from the basal region of scala media 24 hours after electroporation of the guinea-pig cochlea with the CMVp-TRPC3-IRES-dsRed2 cDNA gene construct (Experiment ID Nos. GP13b and GP8/4b).

The electroporation experiments with the CMVp-TRPC3-IRES-DsRed2 construct showed expression of the reporter in four out of six experiments. Of these, four experiments used the basal turn scala tympani electrode as the anode (STb(−)) and expression of the DsRed2 reporter was imaged in three cases. Two experiments utilized a cathode (+) electrode placement in the basal scala vestibuli region, with DsRed2 reporter identified in one of these. For the STb(−) electrode configuration, reporter gene expression was primarily localized to the basal half of the cochlea—in close proximity to the shaped scala tympani electrode. The majority of transfected cells were mesenchymal cells on the lateral aspect of the spiral limbus and the medial aspect of the lateral wall, in the scala tympani compartment (FIG. 2). Limited expression was detected in supporting cells of the organ of Corti. Expression was maintained for the duration of the study (96 hours).

Figure 3:
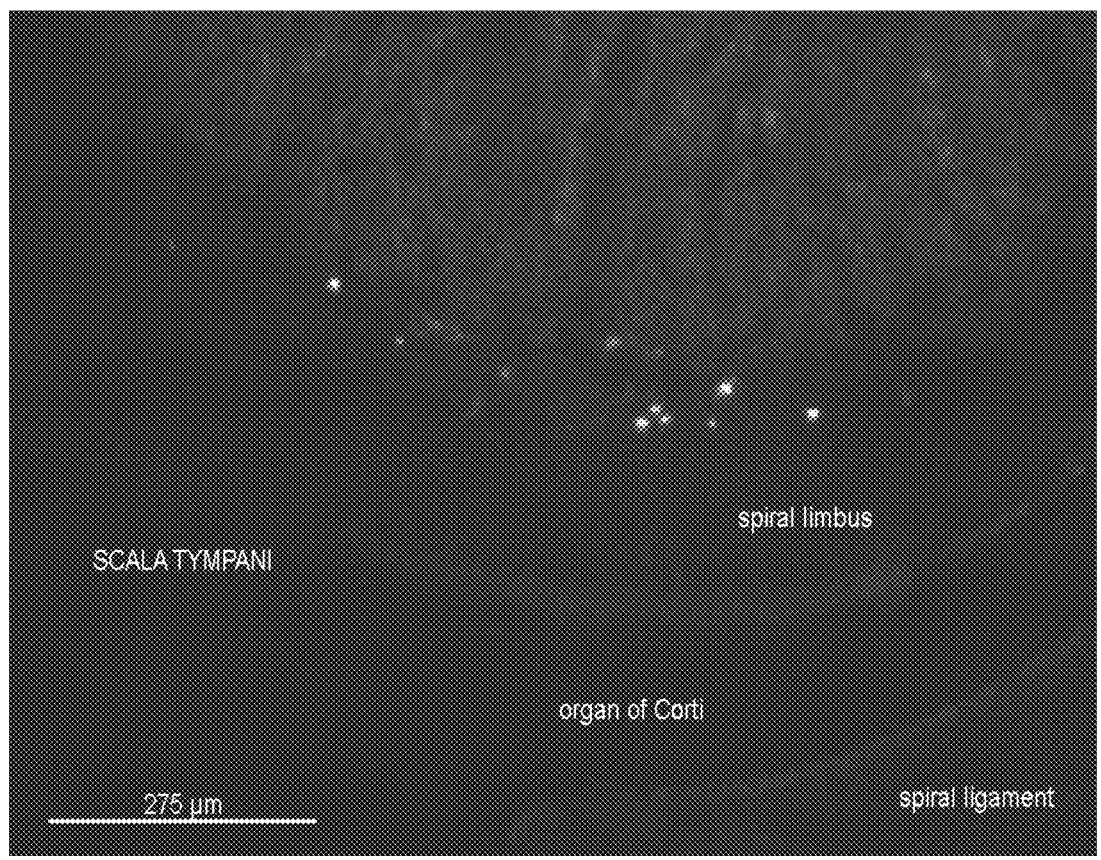
FIG. 3 shows a low-power confocal microscopy image which demonstrates expression of the CMVp-BDNF-FLAGtag-IRES-eGFPn gene cassette over approximately 750 µm in the basal turn of scala tympani, in close proximity to the location of the electroporation electrode. The fluorescent signal represents eGFP-labelled nuclei of cochlear mesenchymal cells in the scala tympani region of the guinea-pig cochlea, on the lateral wall of the spiral limbus, close to the location of the electroporation electrode (Experiment ID No. GP26a, after two days in culture).
Figure 4:
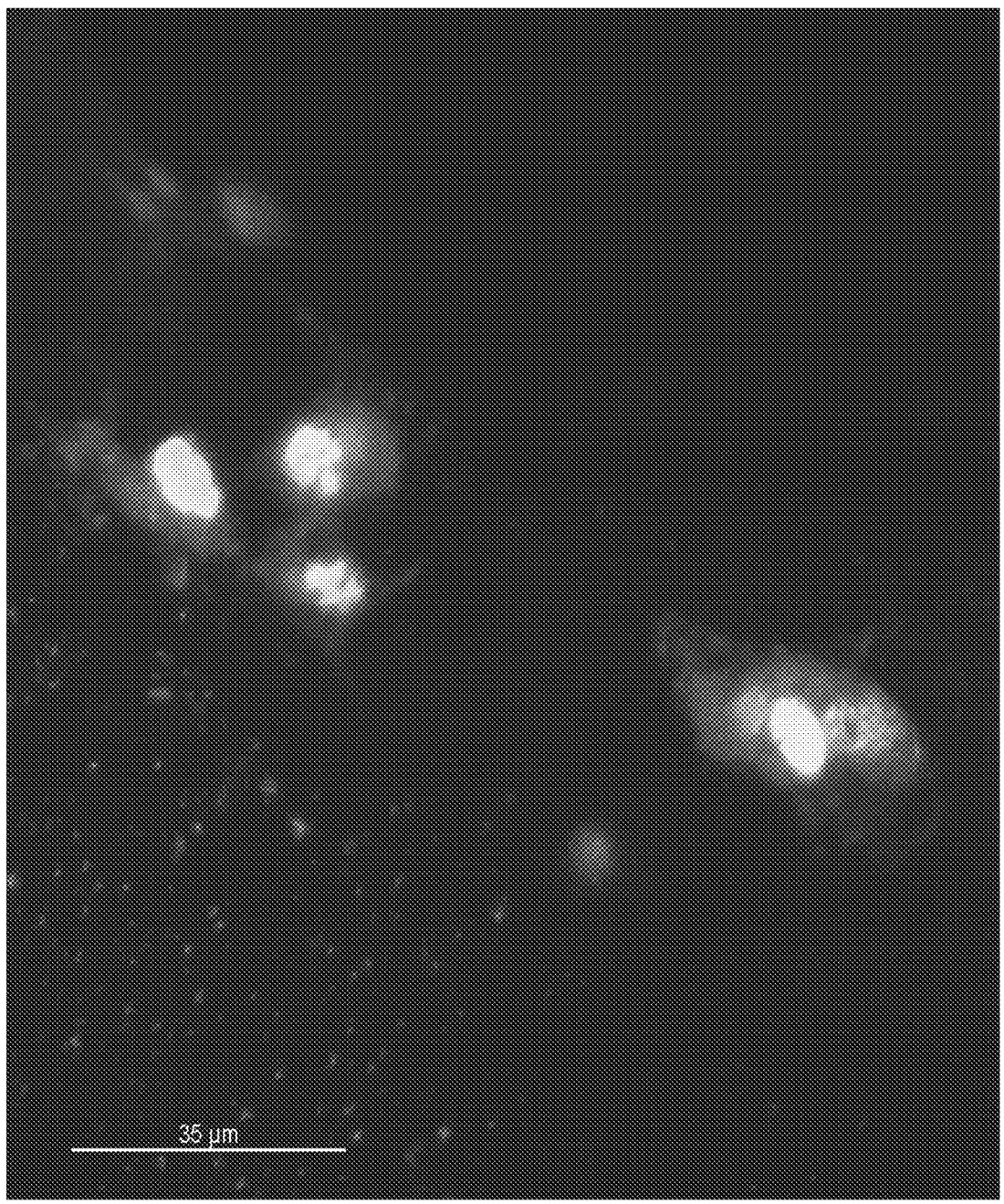
FIG. 4 shows a high-power confocal microscopy image confirming expression of recombinant brain-derived neurotrophic factor (BDNF) by transformed mesenchymal cells within the scala tympani, and represents a detailed image of some of the cells identified by nuclear labelling in FIG. 3. TRITC fluorescence signal in the cytoplasm of cells demonstrates the expression of BDNF polypeptide which is identified by the Flag tag. Fluorescence signal in the nucleus arises from expression of the eGFPn reporter. CMVp-BDNF-FLAGtag-IRES-eGFPn gene cassette (Experiment ID No. GP26a).

A second set of experiments investigated the delivery and heterologous expression of BDNF as a putative therapeutic molecule. Two experiments used the STb(−)-basal anode configuration, and two experiments, the Stb(+) cathode configuration. Expression of the CMVp-BDNF-FLAGtag-IRES-eGFPn construct was confirmed in all four experiments, evident as nuclear GFP labelling, principally within the basal region (turn1 and turn 2; FIG. 3). This expression was sustained for the duration of these experiments (72 hours). Expression of recombinant BDNF by these cells was confirmed by FITC-positive immunolabelling of the cytoplasm of the GFP-positive cells, following fixation and processing for immunofluorescence (FIG. 4).

Both basal anode and cathode electrode configurations produced transfection of the target cells with the transgene.

The anodal configuration for the basal scala tympani electrode was preferred for unipolar electroporation with expression at more apical regions (Turn 3), closer to the apical anode, when the basal cathode configuration was used. In summary, 4 out of 6 experiments using the CMVp-TRPC3-IRES-DsRed2 construct resulted in gene delivery to the cells lining scala media of the cochlea and 4 out of 4 experiments using the CMVp-BDNF-FLAGtag-IRES-eGFPn construct were effective.

TABLE 1

| ID | [cDNA] (µg/µl) & Plasmid (a or b) | Voltage (V) | Pulse width (ms) | # pulses | Pulse interval (s) | Electrode config | Results |
|---|---|---|---|---|---|---|---|
| GP12.aA3 | 1, a | 0 | 0 | 0 | 0 | STb(−); SVb(+) | Control, placement of electrodes but no voltage applied; outcome = N/E |
| GP12.b | 1, a | 10 | 30 | 100 | 10 | STb(−) SVb(+) | +ve GFP, location C2 = T1; D3 = T2, 48 h |
| GP13.a | 1, a | 40 | 50 | 60 | 1 | STb(+) SVb(−) | N/E |
| GP13.b | 1, a | 100 | 50 | 60 | 5 | STb(−) SVb(+) | +ve GFP, location C2 = T4; D3 = T2; D5 = 12; 24 h, 48 h |
| GP8/4a | 0.1, a | 0 | 0 | 0 | 0 | STb(−) A(+) | Control, Lipofectamine 2000 in Opti-MEMI media; N/E |
| GP8/4b | 0.1, a | 100 | 50 | 100 | 5 | STb(−) A(+) | +ve; D2 = T1, many cells; |
| GP9/4a | 0 | 0 | 0 | 0 | 0 | 0 | Control, no DNA |
| GP9/4b | 1, a | 100 | 50 | 100 | 5 | STb(−) A(+) | N/E @ 24 h |
| GP17a | 0 | 0 | 0 | 0 | 0 | — | Control, no DNA; N/E |
| GP17b | 1, a | 100 | 50 | 100 | 5 | Outer spiral limbus(+) A(−) | +ve; C1 = T1; C4 = T2; C5 = T3; 24 hr & 96 hr |
| GP25a | 1, b | 100 | 30 | 100 | 5 | STb(−) A(+) | +ve; A5 = T1; many nuclei GFP +ve; A5 = T1 (fixed for immunofluorescence anti-FLAG = BDNF @ 48 hr); A6 = T1; B2 = T3 lateral wall; B3 = T2 lateral wall; 48 hr; 72 hr, B1 = T1; B3 = T2 lateral wall. |
| GP26a | 1, b | 100 | 50 | 50 | 5 | STb(+) A(−) | +ve; C1 = T1 − T3 lateral wall, nuclei +ve in base − apex; C3 = T1, 20 nuclei +ve on target region (processed for BDNF); C4 = T2; C5 = T2; 72 hrs. |
| GP27a | 1, b | 100 | 50 | 50 | 5 | STb(−) A(+) | +ve; B3 = T1, ST-spiral limbos region, B4 = T2; B5 = T2; 72 hr |
| GP27b | 1, b | 100 | 50 | 50 | 5 | STb(+) A(−) | =ve; C1 = T1 − T2 ST; C5 = T2, 7 nuclei; T1 = T1; 72 hr. |

Key:
plasmid a = CMVp-TRPC3-IRES-DsRed2;
plasmid b = CRAVp-BDNF-FLAG tag-IRES-eGFPn
STb(−), anode inserted into basal turn scale tympani via round window;
SVb(+) cathode inserted into scala vestibule basal turn via oval window;
A(+) cathode into apex of cochlea.
An . . . Cn refers to organotypic culture plate location,
T1 . . . T4 refers to the four turns of the cochlea (base to apex).
N/E = no expression; +ve = expression detected.

These experiments demonstrated the feasibility of electroporation-mediated transfer of naked therapeutic polynucleotides into target tissues in an adult mammalian cochlea. This was achieved through the use of a shaped electrode placed within the scala tympani perilymphatic chamber, as a model for cochlear implant prosthesis. Both unipolar and bipolar electrode configurations for electroporation-based gene delivery in the adult cochlear have been validated by the results achieved using basal-basal and basal-apical electrode placement, as well as both cathode and anode configurations of the scala tympani electroporation electrode. The density of transduced cells was greatest in the tissue immediately adjacent to the basal electroporation electrode, and the numbers of cells expressing the reporter genes decreased in more apical regions of scala tympani. These data indicate the electroporation based gene delivery is efficient and site-specific.

Example 2

Assessment of Neuroprotection Provided by Cochlear Cell Transfection

A guinea-pig model is employed to study the ability of electroporetic transfection of a polynucleotide construct encoding a spiral ganglion trophic factor to support the survival of spiral ganglion neurons.

Cochlear sensory hair cells are destroyed using a single co-administration of kanamycin (400 mg/kg provided subcutaneously) and frusemide (100 mg/kg intravenously, causing a progressive loss of the cochlear (spiral ganglion) neurons in following weeks.

After kanamycin/frusemide treatment, a solution comprising an expression cassette, such as the cassettes described in Example 1, encoding a spiral ganglion cell neurotrophic factor, for example any one of glial cell line-derived neurotrophic factor, brain-derived neurotrophic factor, neurotrophin-3, neurotrophin-4/5, and ciliary neurotrophic factor, is introduced to the cochleae of the anaesthetised guinea pigs. Electrodes inserted into the scala tympani are used to create an electroporetic stimulus to transfect mesenchymal cells of the scala tympani. The electrodes are then removed, the cochleae closed and the animals allowed to recover.

At a series of time points commencing immediately after surgery and at one weekly intervals up to four months, animals are euthanized and tissue sections used to assess spiral ganglion cell numbers, and the outgrowth of spiral ganglion cell neurites towards transfected cochlear cells, as detected via reporter gene expression, by immunolabelling with a florescent anti-neurofilament antibody and/or by detection of therapeutic molecule expression using immunofluorescence.

Example 3

Use of a Cochlear Implant to Transfect Cochlear Cells by Electroporation

Guinea-pigs are deafened by selective lesion of the cochlea hair cells using kanamycin/frusemide as described in Example 2, and undergo chronic cochlear implantation, via the round window for functional validation of the efficacy of cochlear implant-mediated electroporation gene delivery. A nucleic acid molecule which encodes a neurotrophic factor for spiral ganglion neurons, for instance in the form of an expression cassette as described in Example 1 which also comprises a reporter molecule, or which modulates endogenous neurotrophic factor expression is delivered into scala media immediately prior to, or with the implantation of a cochlear implant prosthesis and then electroporation occurs by delivering high field strength current through the cochlear implant prosthesis electrode array. The array is left in place and the wound closed. The nucleic acid molecule is selected from nucleic molecules comprising sequences encoding Neurotrophin-3 (NT-3) or Neurotrophin-3 precursor molecule (NCBI Accession No. HGNC: 8023); Neurotrophin 4/5 (NT-4/5, NT-4, NT-5, NTF4, NTF5) (NCBI Accession No HGNC:8024); Nerve growth factor (NGF) (NCBI Accession No. HGNC:7808); Brain derived neurotrophic factor (BDNF) (NCBI Accession No. HGNC:1033); glial cell line-derived neurotrophic factor (GDNF) (NCBI Accession No. HGNC:4232); ciliary neurotrophic factor (CNTF) (HGNC Accession No. HGNC: 2169; Activity dependent neurotrophic factor gene (ADNF); Apyrase; or ectonucleoside triphosphate diphosphohydrolase 2 (ENTPD2); alpha-melanocyte stimulating hormone (alpha-MSH); bone morphogenetic protein (BMP); Sonic hedgehog; Wnts; Laminin; Netrin-1; Ephrins; slit2/slit3; and Leukaemia inhibitory factor.

The efficacy of the delivery is assessed by recording the electrically evoked potentials arising from direct stimulation of the cochlear implant array in its prosthesis stimulation mode. The electrically evoked auditory brainstem responses are recorded using a differential signal between a subdermal electrode located at the vertex of the skull and a lateral subdermal electrode located adjacent to the temporal bone on the side receiving the cochlear implant. Control experiments omit the nucleic acid molecule with electroporation stimulation, and also include the nucleic acid molecule without electroporation stimulation.

The efficacy of the gene therapy for prevention of spiral ganglion neuron loss and re-growth of the spiral ganglion neurites towards the cochlear implant array is assessed over a period of weeks by determining electrical stimulus threshold strengths and input/output rate functions for the evoked potentials that arise from activity in the cochlear nerve and from the down-stream auditory activity in the brain.

After four months, the guinea pig cochleae are taken and neuronal survival and neurite outgrowth assessed by histochemistry and anti-neurofilament immunofluorescence. Sustained expression of the nucleic acid molecule is detected by the fluorescence reporter detection, or immunofluorescence detection of the reporter protein (anti-GFP antibody).

Example 4

Treatment of Human Subjects

Human subjects are recruited on the basis of sudden onset hearing loss attributable to lesion of the cochlear hair cells, as assessed by loss of distortion product otoacoustic emissions (DPOAE). This condition provides a differential for analysis of long-term neuronal survival and outgrowth of the neurites to the region of the cochlear prosthesis, based on electrically evoked auditory brainstem response (EABR) measurements undertaken post-operatively over a 12 month period.

Cochlear implant surgery will not differ from the standard practice of implantation of the cochlear electrode array via an incision through the round window or cochleostomy, except that immediately prior to insertion of the electrode array, a therapeutic gene construct (cDNA) is introduced into scala tympani using, for example, a fine catheter of equivalent length to the cochlear implant. The cDNA is typically provided at 1 μg/μl concentration in water or in a buffered artificial perilymph with reduced osmolarity (total volume delivered 30 μl).

The catheter is then removed and the cochlear implant's electrode array is inserted. The cochlear implant is then immediately driven in electroporation mode, to deliver a field strength between electrodes of sufficient intensity and duration to produce dialectric breakdown of the cells in closest proximity to the electrodes, which are typically the mesenchymal cells lining scala tympani on the modiolar canal wall. The electroporation stimulus will result in entry of the naked cDNA agent, transfecting the cells. The number of electrical pulses required for this procedure is typically fewer than 250, with a pulse duration of approximately 50 milliseconds, and typically 1 second per pulse. On this basis the electroporation will require less than 10 minutes additional time and could be undertaken while the surgeon continues with the procedure.

Dedicated circuitry in the stimulator unit of the cochlear implant, which is typically surgically implanted in a post-auricular location, is used to drive the electroporation, however in other embodiments separate electroporation electrode nodes on the implant may be used and activated by an external isolated electroporation circuitry for this procedure, and are subsequently disconnected at the completion of the procedure.

The surgical procedure otherwise proceeds as for a conventional cochlear implant procedure and normal activation of the cochlear implant occurs as a conventional post-operative undertaking.

Efficacy of the gene delivery and expression of the therapeutic molecules would be detected if reduced stimulus intensities are required to achieve EABR thresholds or in hearing discrimination testing (audiometry) and audiological assessment of hearing function and speech discrimination. A successful reduction in stimulus intensities required for hearing threshold (compared with controls) would indicate that spiral ganglion cell neurites are in closer proximity to the cochlear implant, and this would be a positive indicator for neural protection and neural repair (neuritogenesis) arising from the neurotrophic stimulation.

Refinements of the cochlear implant array for cochlear implants may be possible in the light of increased neurite proximity to the implant which may be achieved following the methods of the invention.

What is claimed is:

1. A cochlear implant, comprising:
auditory nerve stimulator circuitry to generate an auditory nerve stimulator electrical pulse profile;
a linear array of electrodes configured as a series of independently addressable nodes along a length of the cochlear implant which lies within the cochlea, each of the series of independently addressable nodes coupled to the auditory nerve stimulator circuitry for providing the auditory nerve stimulator electrical pulse profile to the cochlea; and
electroporation-driving circuitry, separate from the auditory nerve stimulator circuitry, coupled to a plurality of the independently addressable nodes of the linear array of electrodes of the cochlear implant for electroporation using one or more electrodes as anodes and one or more other electrodes interspersed along the linear electrode array as cathodes for electroporation current delivery such that the cochlear implant can generate an electroporation mode electrical pulse profile delivering high field strength current, and
provide the electroporation electrical pulse profiles to the cochlea via the plurality of addressable nodes to transfect cells along the length of the linear array.

2. The cochlear implant of claim 1, wherein the implant comprises a lumen or channel for delivery of an agent to the cochlea.

3. The cochlear implant of claim 2, wherein the agent comprises a nucleic acid module encoding a neurotropic factor for spiral ganglion cells.

4. The cochlear implant of claim 3, wherein the neurotropic factor is selected from any one of Neurotrophin-3, Neurotrophin-3 precursor molecule, Neurotrophin 4/5, Nerve growth factor, Brain-derived neurotrophic factor, glial cell line-derived neurotrophic factor, ciliary neurotrophic factor and Activity dependent neurotrophic factor.

5. The cochlear implant of claim 1, wherein groups of nodes of said cochlear implant are driven together to act as one electrode for electroporation.

6. The cochlear implant of claim 1, wherein said electroporation mode electrical pulse profile is provided with a voltage of from 10 to 100 volts.

7. The cochlear implant of claim 1, wherein polarity of individual nodes is altered over time during electroporation.

8. The cochlear implant of claim 1, wherein the electroporation-driving circuitry is configured to deliver a square wave or ramped electroporation stimulus of from 100 μs to 500 ms duration, optionally 30 ms duration.

9. The cochlear implant of claim 1, wherein the electroporation-driving circuitry is configured to deliver said electroporation stimulus in from 25 to 200 pulses, optionally, 50 to 100 pulses, with intervals between pulses of 1, 2, 3, 4, 5, 6, 7, 8, 9, or 10 seconds.

10. An electroporation apparatus for transfecting cells of the cochlea with an agent, the apparatus comprising:
an electroporation electrode array shaped to model a cochlear implant prosthesis configured for temporary insertion into the cochlear for performing electroporation and subsequently removed, the electroporation electrode array being electrically conductive at its surface along one or more portions of the entire length of the electrode, and electrically non-conductive at its surface along other portions of its length to provide a linear array of two or more contiguous electrodes, without tissue in between, to be driven as anodes and cathodes for electroporation; and
external electroporation-driving circuitry connected to the electrodes of the electroporation electrode array and configured to provide electroporation electrical pulse profiles having a square wave or ramped electroporation stimulus with pulse width from 100 μs to 500 ms and a voltage of at least 10 volts via the electroporation electrode array, to drive the electrodes in the linear array as anodes and cathodes to generate an electric field adjacent the array to transfect cells in tissue adjacent the linear array.

11. The electroporation apparatus as claimed in claim 10, wherein the non-conductive portions are insulated at the surface of the electrode with a coating.

12. The electroporation apparatus as claimed in claim 10 wherein the electrode comprises a lumen or channel for delivery of an agent to the cochlea.

13. The electroporation apparatus as claimed in claim 12, wherein the agent comprises a nucleic acid module encoding a neurotropic factor for spiral ganglion cells.

14. The electroporation apparatus as claimed in claim 13, wherein the neurotropic factor is selected from any one of Neurotrophin-3, Neurotrophin-3 precursor molecule, Neurotrophin 4/5, Nerve growth factor, Brain-derived neurotrophic factor, glial cell line-derived neurotrophic factor, ciliary neurotrophic factor and Activity dependent neurotrophic factor.

15. The electroporation apparatus of claim 10, wherein the electroporation electrode array comprises a lumen or channel for delivery of an agent.

* * * * *

UNITED STATES PATENT AND TRADEMARK OFFICE
CERTIFICATE OF CORRECTION

PATENT NO. : 11,026,842 B2
APPLICATION NO. : 15/387344
DATED : June 8, 2021
INVENTOR(S) : Gary David Housley It is certified that error appears in the above-identified patent and that said Letters Patent is hereby corrected as shown below:

In the Claims

In Column 28, Lines 36-37, in Claim 10, after "prosthesis", delete "configured for temporary insertion into the cochlear"

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*